United States Patent [19]

Sato et al.

[11] Patent Number: 4,540,654
[45] Date of Patent: Sep. 10, 1985

[54] METHOD OF FORMING COLOR IMAGE COMPRISING HETEROCYCLIC MAGENTA DYE-FORMING COUPLER

[75] Inventors: Tadahisa Sato; Toshio Kawagishi; Nobuo Furutachi, all of Kanagawa, Japan

[73] Assignee: Fuji Photo Film Co., Ltd., Kanagawa, Japan

[21] Appl. No.: 590,818

[22] Filed: Mar. 19, 1984

[30] Foreign Application Priority Data

Mar. 18, 1983 [JP] Japan .................... 58-45512

[51] Int. Cl.$^3$ .................... G03C 7/00; G03C 1/40; G03C 7/40
[52] U.S. Cl. .................... 430/381; 430/384; 430/385; 430/548; 430/558
[58] Field of Search ................ 430/381, 384, 385, 548, 430/558

[56] References Cited

U.S. PATENT DOCUMENTS 3,725,067  4/1973  Bailey et al. ............ 430/558 X
3,770,447 11/1973  Boie et al. ............. 430/558
4,338,393  7/1982  Bailey et al. ............ 430/548 X

FOREIGN PATENT DOCUMENTS 1810463 10/1970  Fed. Rep. of Germany .

OTHER PUBLICATIONS

Research Disclosure, "Hetrocyclic Magenta Dye--Forming Couplers", pp. 345-346, Sep. 1981.

Primary Examiner—John E. Kittle
Assistant Examiner—Mukund J. Shah
Attorney, Agent, or Firm—Sughrue, Mion, Zinn, Macpeak, and Seas

[57] ABSTRACT

A method of forming a color image comprising developing a silver halide photographic light-sensitive material with a developing solution containing an aromatic primary amine is disclosed. The developing is carried out in the presence of a coupler represented by the general formula (I) described below and/or a polymer coupler which is a polymer or copolymer having a repeating unit derived from a vinyl monomer containing a part represented by the general formula (I) described below in its molecule:

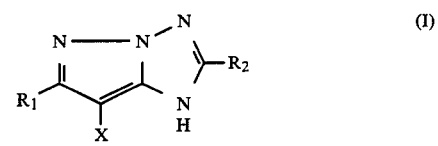

(I)

wherein $R_1$ and $R_2$, which may be the same or different, each represents a hydrogen atom or a substituent; and X represents a hydrogen atom or a group capable of being released upon coupling.

The magenta color forming coupler represented by the general formula (I) or the polymer coupler containing the part represented by the general formula (I) has a good color forming property and provides a magenta color image having an excellent spectral absorption property free from subsidiary absorptions in the region around 430 nm and good fastness. A silver halide photographic light-sensitive material containing the magenta coupler is also disclosed.

24 Claims, 1 Drawing Figure

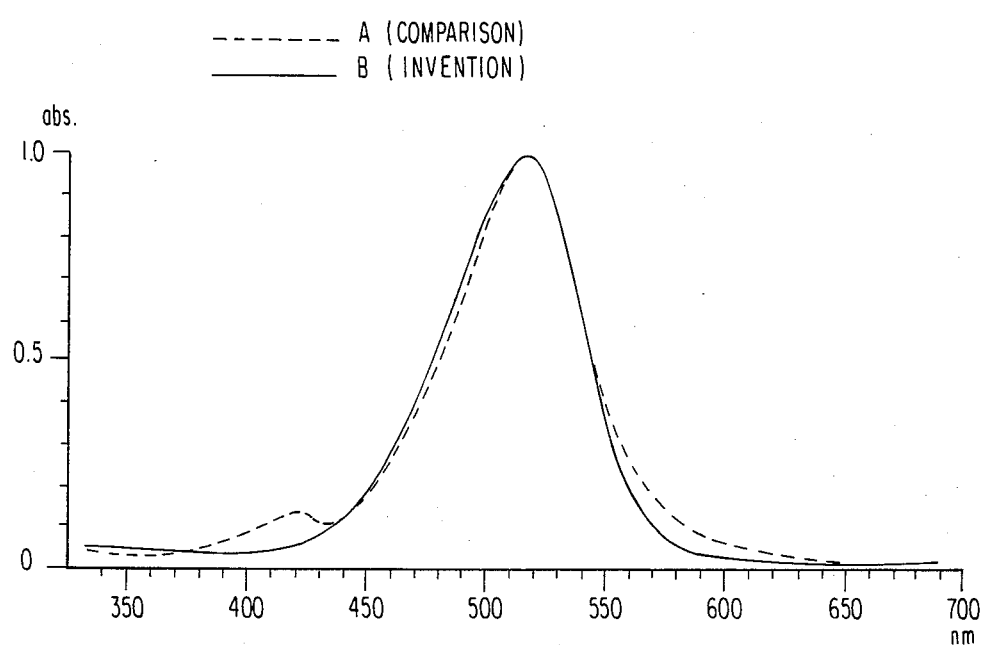

METHOD OF FORMING COLOR IMAGE COMPRISING HETEROCYCLIC MAGENTA DYE-FORMING COUPLER

FIELD OF THE INVENTION

The present invention relates to a novel method of forming a magenta color image upon a coupling reaction with an oxidation product of an aromatic primary amine formed by oxidation with silver halide. More particularly, it relates to a method of forming a color image utilizing a novel magenta coupler, i.e., a 1H-pyrazolo[1,5-b]-1,2,4-triazole.

BACKGROUND OF THE INVENTION

It is well known that an oxidized aromatic primary amine color developing agent formed by oxidation with exposed silver halide reacts with a coupler to form a dye such as an indophenol, an indoaniline, indamine, an azomethine, a phenoxazine, a phenazine and the like, thus forming a color image.

In order to form a magenta color image, a 5-pyrazolone type coupler, a cyanoacetophenone type coupler, an indazolone type coupler, a pyrazolobenzimidazole type coupler or a pyrazolotriazole type coupler is employed.

Magenta color image forming couplers which have been widely used in practice and on which various investigations have been made are generally 5-pyrazolones. It is known that dyes formed from 5-pyrazolone type couplers are excellent in fastness to heat and light but they have the undesirable absorption of yellow in the region around 430 nm which causes color turbidity.

In order to reduce the yellow component, a pyrazolobenzimidazole nucleus as described in British Pat. No. 1,047,612, an indazolone nucleus as described in U.S. Pat. No. 3,770,447 and a pyrazolotriazole nucleus as described in U.S. Pat. No. 3,725,067 have been proposed as a magenta color image forming coupler skeleton. However, the magenta couplers described in these patents are still insufficient since they provide only poor color images when they are mixed with a silver halide emulsion in the form of a dispersion in a hydrophilic protective colloid such as gelatin, they have a low solubility in an organic solvent having a high boiling point, they have some difficulties in synthesis thereof, or they have a relatively low coupling activity in conventional developing solutions.

The present inventors have carried out extensive investigations on a novel magenta color image forming couplers free from the subsidiary absorptions in the regions around 430 nm which is the most disadvantageous point in view of spectral absorption characteristics of a dye formed from 5-pyrazolone type magenta couplers. As a result, the present inventors have found a certain group of couplers which provide a color image without a subsidiary absorption in a shorter wavelength side of the main absorption and which have good fastness and which can be easily synthesized.

SUMMARY OF THE INVENTION

Therefore, an object of the present invention is to provide a novel class of magenta color image forming couplers which have an excellent color reproducibility, color forming rate and maximum color density, which are advantageous with repect to their synthesis and which can prepare the so-called 2-equivalent couplers by introducing a releasing group into their coupling active sites whereby the amount of silver needed can be reduced.

Another object of the present invention is to provide a method of forming a magenta color image utilizing such magenta color image forming couplers.

Other objects of the present invention will become apparent from the following detailed description and examples.

These objects of the present invention are achieved by a method of forming a color image comprising developing a silver halide photographic light-sensitive material with a developing solution containing an aromatic primary amine in the presence of a coupler represented by the general formula (I) described below and/or a polymer coupler which is a polymer or copolymer having a repeating unit derived from a vinyl monomer containing a part represented by the general formula (I) described below in its molecule.

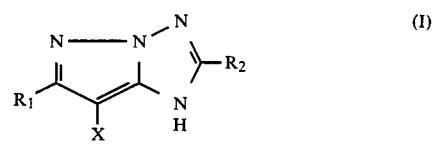

wherein $R_1$ and $R_2$, which may be the same or different, each represents a hydrogen atom or a substituent; and X represents a hydrogen atom or a group capable of being released upon coupling.

BRIEF DESCRIPTION OF THE ACCOMPANYING DRAWING

The FIGURE is a graph showing the absorption spectra of dyes formed from Comparison Coupler A (Curve A) and Coupler (1) according to the present invention (Curve B) in the manner as described in Example 1, respectively.

DETAILED DESCRIPTION OF THE INVENTION

In the above-described general formula (I), $R_1$ and $R_2$ each preferably represents a hydrogen atom, a halogen atom, an aliphatic residue, an aryl group, a heterocyclic group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclicoxy group, an acyloxy group, a carbamoyloxy group, a silyloxy group, an aryloxycarbonylamino group, an imido group, a heterocyclicthio group, a sulfinyl group, a phosphonyl group, an aryloxycarbonyl group, an acyl group or an alkoxycarbonyl group; and X preferably represents a hydrogen atom, a halogen atom, a carboxyl group or a group capable of being released upon coupling which is bonded to the carbon atom of the coupling position through an oxygen atom, a nitrogen atom, a carbon atom or a sulfur atom. Further, $R_1$, $R_2$ or X may be a divalent group to form a bis coupler. Moreover, when the part represented by the general formula (I) is included in a vinyl monomer, either $R_1$ or $R_2$ represents a simple bond or a linking group through which the part represented by the general formula (I) is bonded to the vinyl group.

In more detail, $R_1$ and $R_2$ each represents a hydrogen atom; a halogen atom (for example, a chlorine atom, a bromine atom, etc.); an aliphatic residue including a straight chain or branched chain alkyl group having from 1 to 32 carbon atoms, an aralkyl group, an alkenyl group, an alkinyl group, a cycloalkyl group and a cycloalkenyl group, which may be substituted with a substituent bonded through an oxygen atom, a nitrogen atom, a sulfur atom or a carbonyl group, a hydroxy group, an amino group, a nitro group, a carboxy group, a cyano group or a halogen atom (for example, a methyl group, a propyl group, a t-butyl group, a trifluoromethyl group, a tridecyl group, a 2-methanesulfonylethyl group, a 3-(3-pentadecylphenoxy)propyl group, a 3-{4-{2-[4-(4-hydroxyphenylsulfonyl)phenoxy]dodecaneamido}phenyl}propyl group, a 2-ethoxytridecyl group, a trifluoromethyl group, a cyclopentyl group, a 3-(2,4-di-t-amylphenoxy)propyl group, etc.); an aryl group (for example, a phenyl group, a 4-t-butylphenyl group, a 2,4-di-t-amylphenyl group, a 4-tetradecanamidophenyl group, etc.); a heterocyclic group (for example, a 2-furyl group, a 2-thienyl group, a 2-pyrimidinyl group, a 2-benzothiazolyl group, etc.); a cyano group; an alkoxy group (for example, a methoxy group, an ethoxy group, a 2-methoxyethoxy group, a 2-dodecylethoxy group, a 2-methanesulfonylethoxy group, etc.); an aryloxy group (for example, a phenoxy group, a 2-methylphenoxy group, a 4-t-butylphenoxy group, etc.); an acylamino group (for example, an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.); an anilino group (for example, a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-(butyl-4-hydroxyphenoxy)-dodecanamido]anilino group, etc.); a ureido group (for example, a phenylureido group, a methylureido group, an N,N-dibutylureido group, etc.); a sulfamoylamino group (for example, an N,N-dipropylsulfamoylamino group, an N-methyl-N-decylsulfamoylamino group, etc.); an alkylthio group (for example, a methylthio group, an octylthio group, a tetradecylthio group, a 2-phenoxyethylthio group, a 3-phenoxypropylthio group, a 3-(4-t-butylphenoxy)propylthio group, etc.); an arylthio group (for example, a phenylthio group, a 2-butoxy-5-t-octylphenylthio group, a 3-pentadecylphenylthio group, a 2-carboxyphenylthio group, a 4-tetradecanamidophenylthio group, etc.); an alkoxycarbonylamino group (for example, a methoxycarbonylamino group, a tetradecyloxycarbonylamino group, etc.); a sulfonamido group (for example, a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.); a carbamoyl group (for example, an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-t-amylphenoxy)propyl]carbamoyl group, etc.); a sulfamoyl group (for example, an N-ethylsulfamoyl group, an N,N-dipropylsulfamoyl group, an N-(2-dodecyloxyethyl)sulfamoyl group, an N-ethyl-N-dodecylsulfamoyl group, an N-N-diethylsulfamoyl group, etc.); an sulfonyl group (for example, a methanesulfonyl group, an octanesulfonyl group, a benzenesulfonyl group, a toluenesulfonyl group, etc.); an alkoxycarbonyl group (for example, a methoxycarbonyl group, a butyloxycarbonyl group, a dodecyloxycarbonyl group, an octadecyloxycarbonyl group, etc.); a heterocyclicoxy group (for example, a 1-phenyltetrazole-5-oxy group, 2-tetrahydropyranyloxy group, etc.); an acyloxy group (for example, an acetoxy group, etc.); a carbamoyloxy group (for example, an N-methylcarbamoyloxy group, an N-phenylcarbamoyloxy group, etc.); a silyloxy group (for example, a trimethylsilyloxy group, a dibutylmethylsilyloxy group, etc.); an aryloxycarbonylamino group (for example, a phenoxycarbonylamino group, etc.); an imido group (for example, an N-succinimido group, an N-phthalimido group, a 3-octadecenylsuccinimido group, etc.); a heterocyclicthio group (for example, a 2-benzothiazolylthio group, a 2,4-diphenoxy-1,3,5-triazole-6-thio group, a 2-pyridylthio group, etc.); a sulfinyl group (for example, a dodecanesulfinyl group, a 3-pentadecylphenylsulfinyl group, a 3-phenoxypropylsulfinyl group, etc.); a phosphonyl group (for example, a phenoxyphosphonyl group, an octyloxyphosphonyl group, a phenylphosphonyl group, etc.); an aryloxycarbonyl group (for example, a phenoxycarbonyl group, etc.); or an acyl group (for example, an acetyl group, a 3-phenylpropanoyl group, a benzoyl group, a 4-dodecyloxybenzoyl group, etc.). In the substituents $R_1$ and $R_2$, an alkyl group or an alkyl moiety contains 1 to 32 carbon atoms, and an aryl group or an aryl moiety contains 6 to 32 carbon atoms.

X represents a hydrogen atom; a halogen atom (for example, a chlorine atom, a bromine atom, an iodine atom, etc.); a carboxy group, a group bonded to the coupling position through an oxygen atom (for example, an acetoxy group, a propanoyloxy group, a benzoyloxy group, a 2,4-dichlorobenzoyloxy group, an ethoxyoxaloyloxy group, a pyruvyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.); a group bonded to the coupling position through a nitrogen atom (for example, a benzenesulfonamido group, an N-ethyltoluenesulfonamido group, a pentafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzyl-5-ethoxy-3-hydantoinyl group, a 2N-1,1-dioxo-3(2H)-oxo-1,2-benzisothiazolidin-2-yl group, a 2-oxy-1,2-dihydro-1-pyridinyl group, an imidazolyl group, a pyrazolyl group, a 3,5-diethyl-1,2,4-triazol-1-yl group, a 5- or 6-bromobenzotriazol-1-yl group, a 5-methyl-1,2,3,4-tetrazol-1-yl group, a benzimidazolyl group, a 4-methoxyphenylazo group, a 4-pivaloylaminophenylazo group, a 2-hydroxy-4-propanoylphenylazo group, etc.); a group bonded to the coupling position through a sulfur atom (for example, a phenylthio group, a 2-carboxyphenylthio group, a 2-methoxy-5-t-octylphenylthio group, a 4-methanesulfonylphenylthio group, a 4-octanesulfonamidophenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, a thiocyano group, an N,N-diethylthiocarbonylthio group, a dodecyloxythiocarbonylthio group, etc.); or a group bonded to the coupling position through a carbon atom (for example, a triphenylmethyl group, a hydroxymethyl group, an N-morpholinomethyl group, a group represented by the following formula:

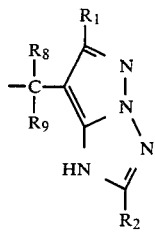

wherein $R_8$ and $R_9$ each represents a hydrogen atom, an alkyl group, an aryl group or a heterocyclic group; and $R_1$ and $R_2$ each has the same meaning as defined hereinbefore, etc.). In the substituents $R_8$ and $R_9$, an alkyl group contains 1 to 18 carbon atoms and an aryl group contains 6 to 18 carbon atoms.

The cases wherein $R_1$, $R_2$ or X represents a divalent group to form a bis coupler are described in more detail hereinafter. In such cases, $R_1$ and $R_2$ each represents a substituted or unsubstituted alkylene group (for example, a methylene group, an ethylene group, a 1,10-decylene group, —CH$_2$CH$_2$—O—CH$_2$CH$_2$—, etc.); a substituted or unsubstituted phenylene group (for example, a 1,4-phenylene group, a 1,3-phenylene group

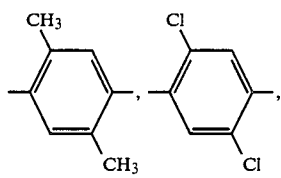

etc.); a group of the formula: —NHCO—R$_3$—CONH— (wherein R$_3$ represents a substituted or unsubstituted alkylene group or a substituted or unsubstituted phenylene group) including, for example, —NHCOCH$_2$CH$_2$CONH—,

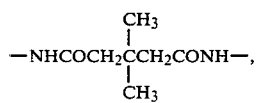

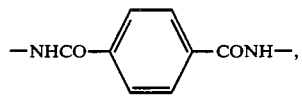

etc.; or a group of the formula: —S—R$_3$—S— (wherein R$_3$ is the same meaning as defined above) including, for example, —SCH$_2$CH$_2$S—,

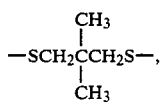

etc.; and X represents a divalent group appropriately formed from the monovalent group for X described above.

The linking group represented by $R_1$ or $R_2$ in the cases wherein the part represented by the general formula (I) is included in a vinyl monomer include an alkylene group including a substituted alkylene group (for example, a methylene group, an ethylene group, a 1,10-decylene group, —CH$_2$CH$_2$OCH$_2$CH$_2$—, etc.); a phenylene group including a substituted phenylene group (for example, a 1,4-phenylene group, a 1,3-phenylene group,

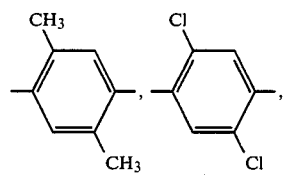

etc.); —NHCO—; —CONH—; —O—; —OCO—; an aralkylene group (for example,

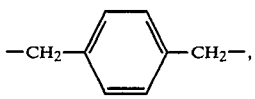

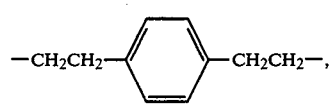

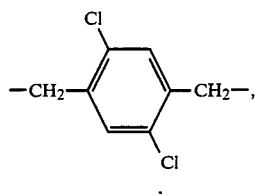

etc.) or a combination thereof.

Specific examples of preferred linking groups are set forth below.
—NHCO—,
—CH$_2$CH$_2$—,

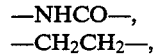

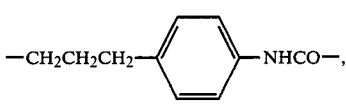

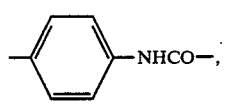

—CH$_2$CH$_2$NHCO—,

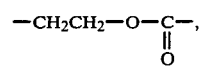

—CONH—CH$_2$CH$_2$NHCO—,
—CH$_2$CH$_2$O—CH$_2$CH$_2$—NHCO—,

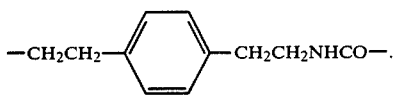

A vinyl group in the vinyl monomer may have a substituent other than the partial group represented by the general formula (I). Preferred examples of such a substituent include a halogen atom or a lower alkyl group having from 1 to 4 carbon atoms (for example, a methyl group, an ethyl group, etc.).

The vinyl monomer containing the part represented by the general formula (I) may be used together with a non-color-forming ethylenic monomer which does not couple with the oxidation product of an aromatic primary amine developing agent to form a copolymer.

Examples of the non-color-forming monomer which does not couple with the oxidation product of an aromatic primary amine developing agent include an acrylic acid (for example, acrylic acid, α-chloroacrylic acid, an α-alkylacrylic acid such as methacrylic acid, etc.), an ester or an amide derived from an acrylic acid (for example, acrylamide, n-butylacrylamide, t-butylacrylamide, diacetoneacrylamide, methacrylamide, methyl acrylate, ethyl acrylate, n-propyl acrylate, n-butyl acrylate, t-butyl acrylate, isobutyl acrylate, 2-ethylhexyl acrylate, n-octyl acrylate, lauryl acrylate, methyl methacrylate, ethyl methacrylate, n-butyl methacrylate, β-hydroxyethyl methacrylate, methylene bisacrylamide, etc.), a vinyl ester (for example, vinyl acetate, vinyl propionate, vinyl laurate, etc.), acrylonitrile, methacrylonitrile, an aromatic vinyl compound (for example, styrene and a derivative thereof, for example, vinyl toluene, divinyl benzene, vinyl acetophenone, sulfo styrene, etc.), itaconic acid, citraconic acid, crotonic acid, vinylidene chloride, a vinyl alkyl ether (for example, vinyl ethyl ether, etc.), maleic acid, maleic anhydride, an ester of maleic acid, N-vinyl-2-pyrrolidone, N-vinyl pyridine, 2- or 4-vinyl pyridine, etc. Two or more non-color-forming ethylenically unsaturated monomers described above can be used together. For example, a combination of n-butyl acrylate and methyl acrylate, styrene and methacrylic acid, methacrylic acid and acrylamide, methyl methacrylate and diacetoneacrylamide, etc., can be employed.

The non-color-forming ethylenically unsaturated monomer which is used to copolymerize with a solid water-insoluble monomer coupler can be selected so that the copolymer to be formed possesses good physical properties and/or chemical properties, for example, solubility, compatibility with a binder such as gelatin in a photographic colloid composition, flexibility, heat stability, etc., as is well known in the field of polymer color couplers.

Polymer couplers which can be used in the present invention may be water-soluble couplers or water-insoluble couplers. Particularly, polymer couplers in the form of a latex are preferably used.

Specific examples of the representative magenta couplers according to the present invention are set forth below, but the present invention should not be construed as being limited thereto.

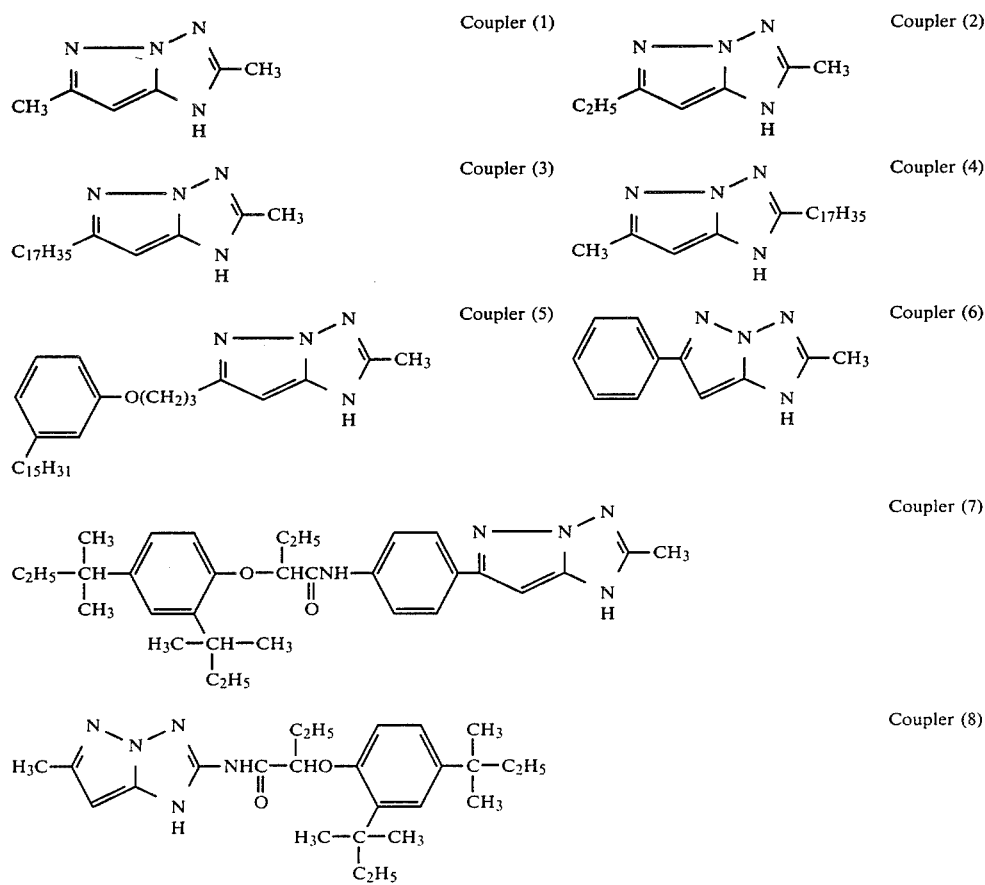

-continued
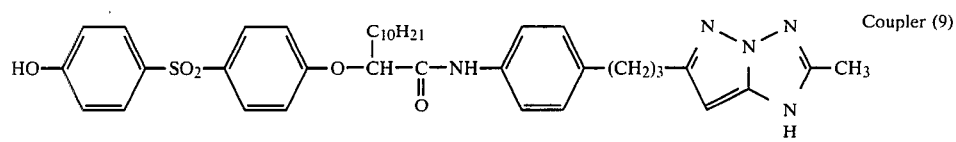
Coupler (9)
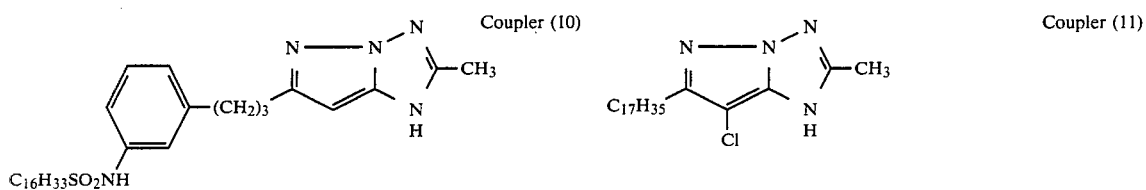
Coupler (10)　　Coupler (11)
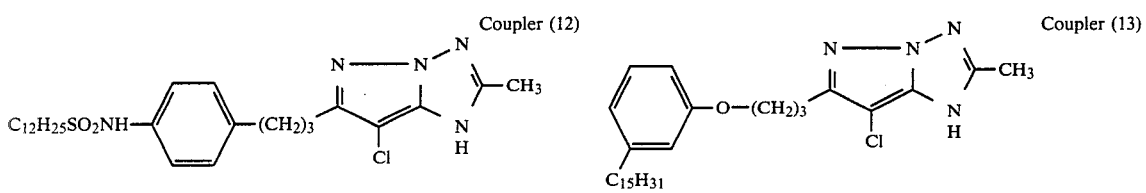
Coupler (12)　　Coupler (13)
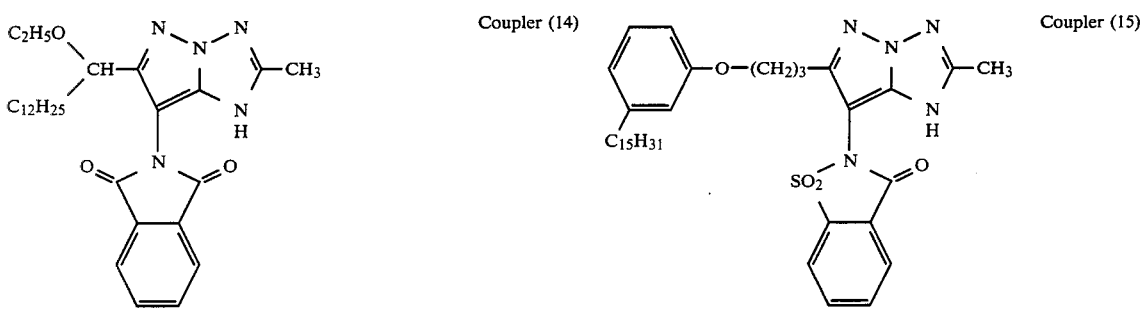
Coupler (14)　　Coupler (15)
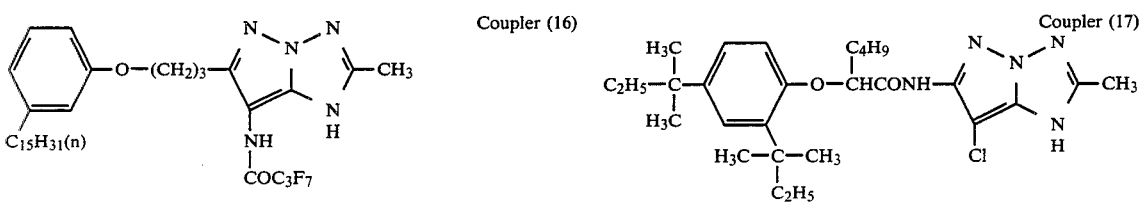
Coupler (16)　　Coupler (17)
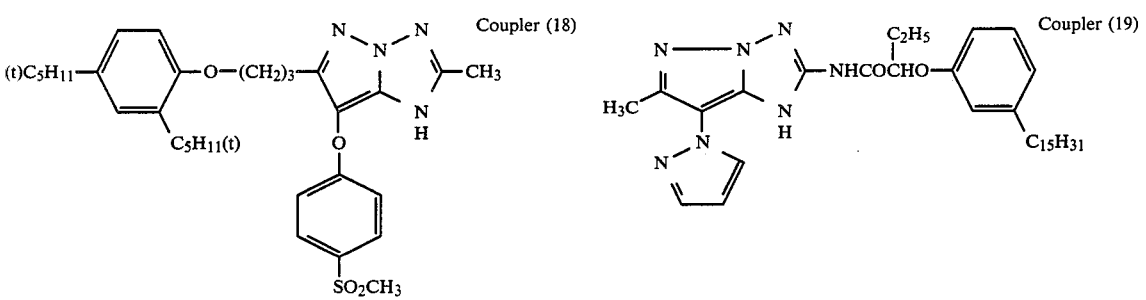
Coupler (18)　　Coupler (19)

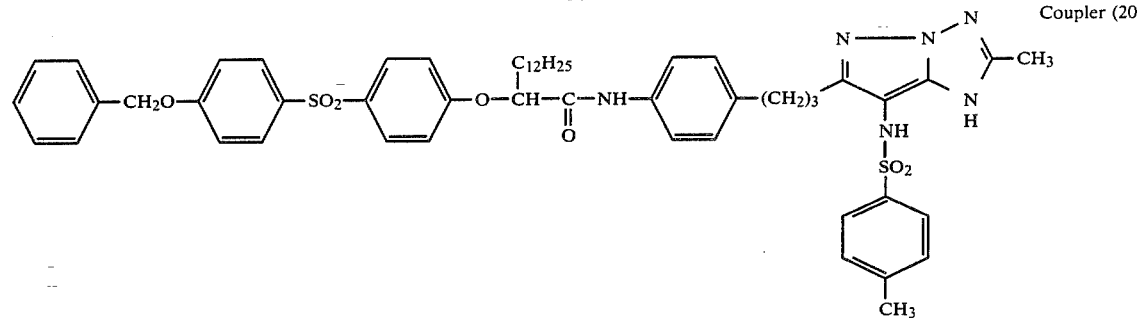
Coupler (20)
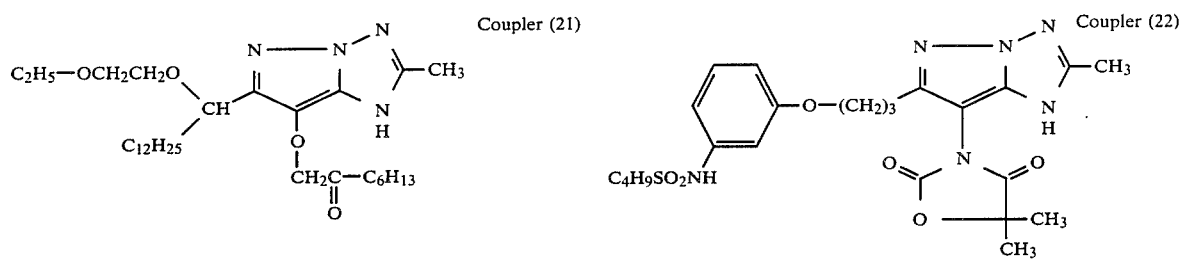
Coupler (21)  Coupler (22)
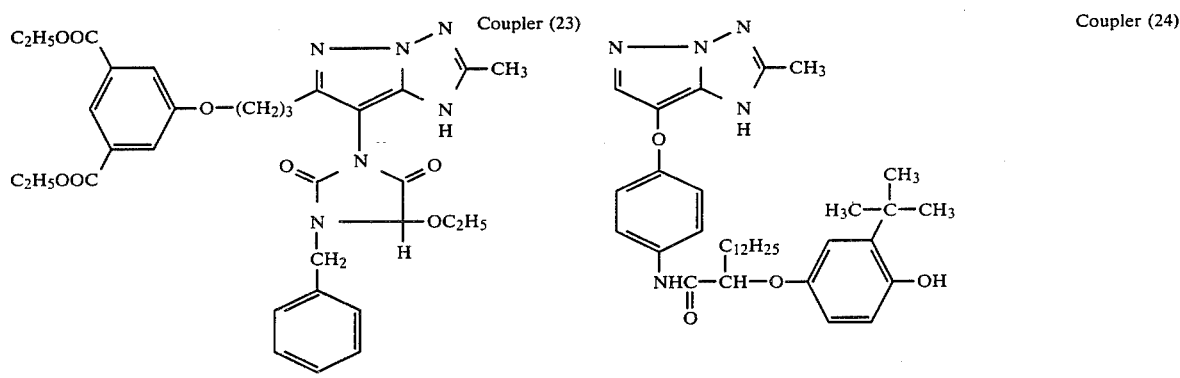
Coupler (23)  Coupler (24)
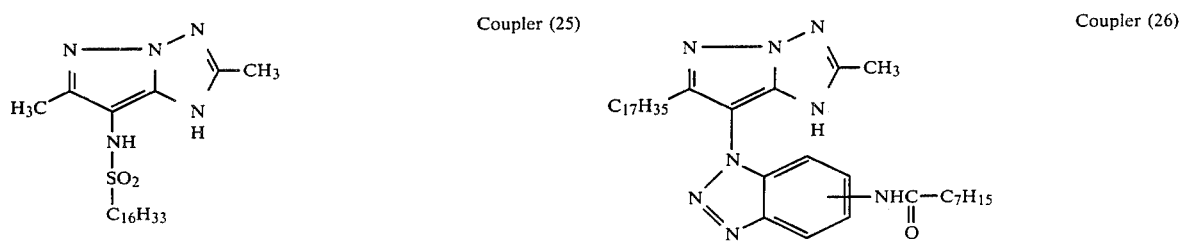
Coupler (25)  Coupler (26)
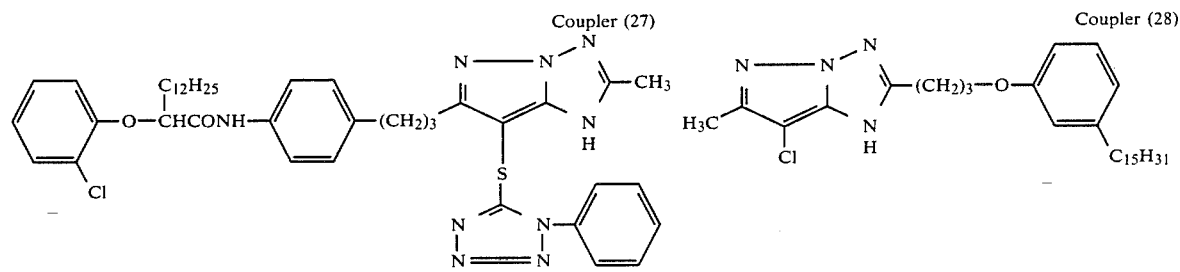
Coupler (27)  Coupler (28)
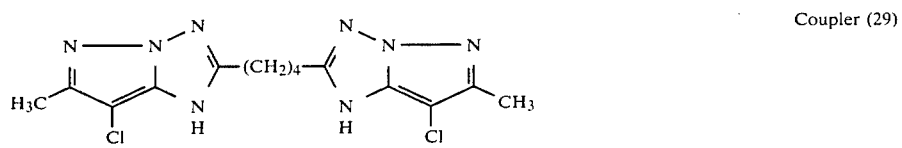
Coupler (29)

Coupler (30)
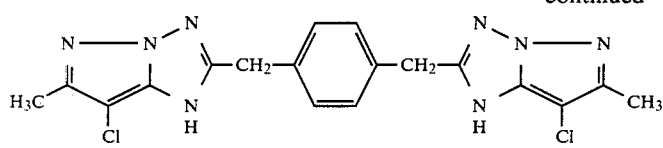
Coupler (31)
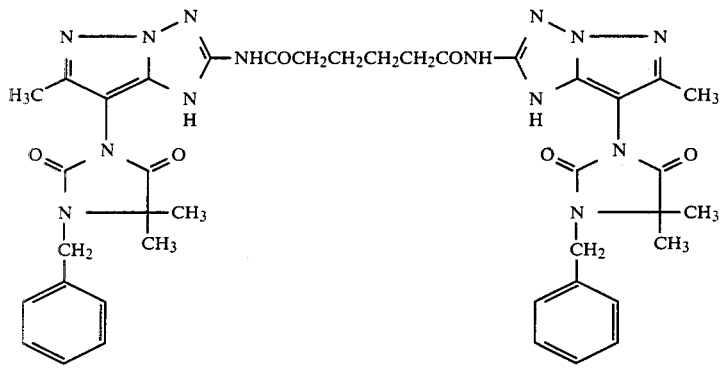
Coupler (32)
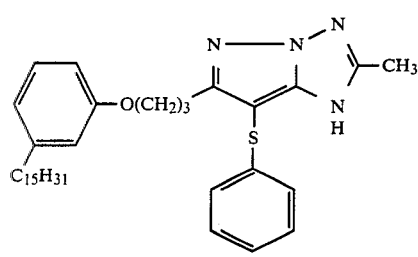
Coupler (33)
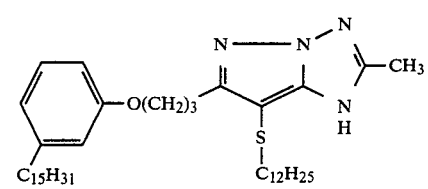
The following three examples (i.e., Couplers (34), (35) and (36) are specific examples of monomer coupler according to the present invention.
Coupler (34)
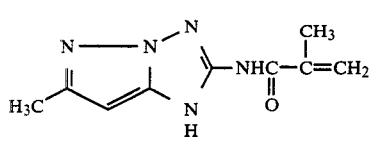
Coupler (35)
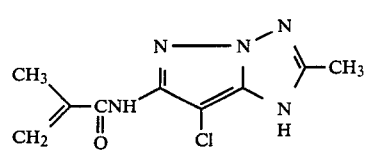
Coupler (36)
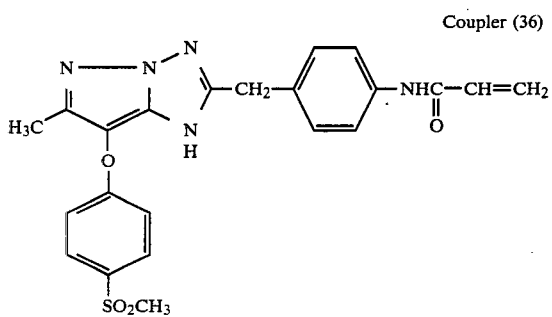
Coupler (37)
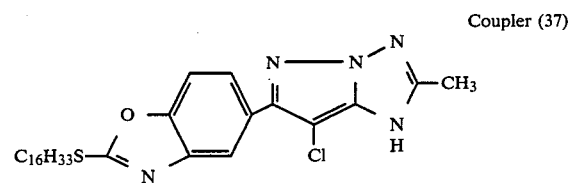
Coupler (38)
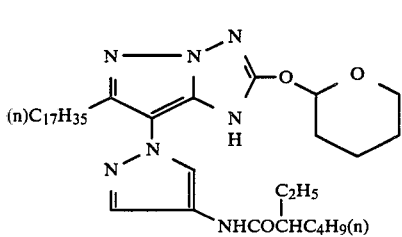

-continued
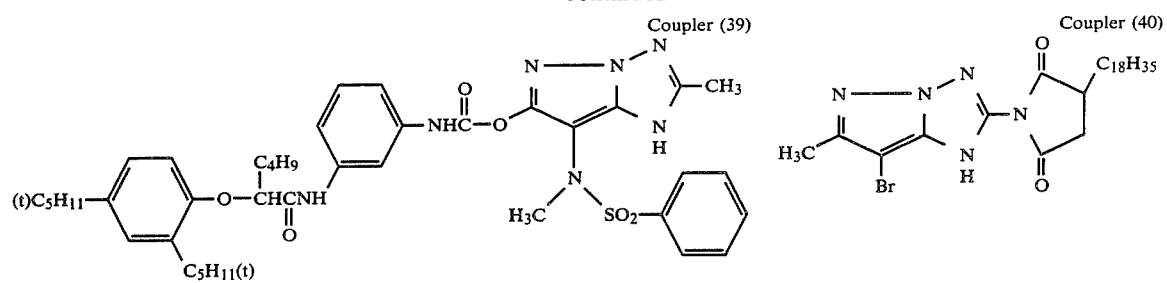
Coupler (39)
Coupler (40)
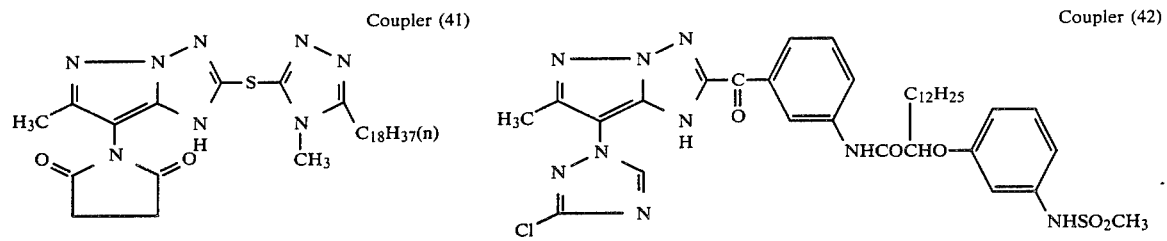
Coupler (41)
Coupler (42)
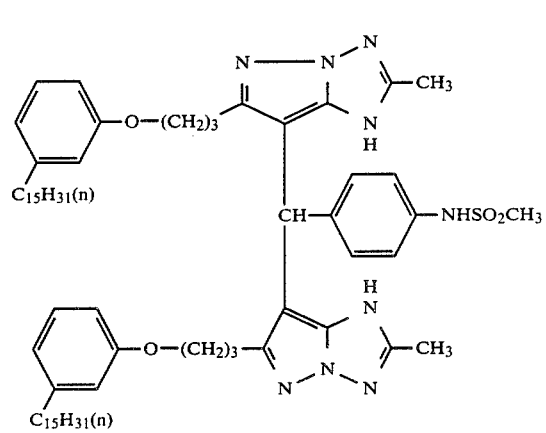
Coupler (43)
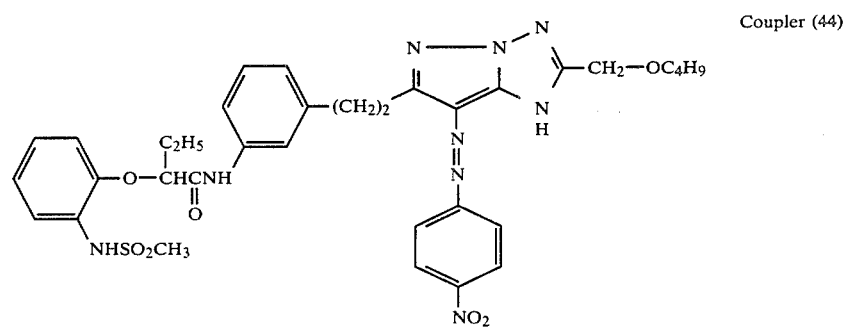
Coupler (44)
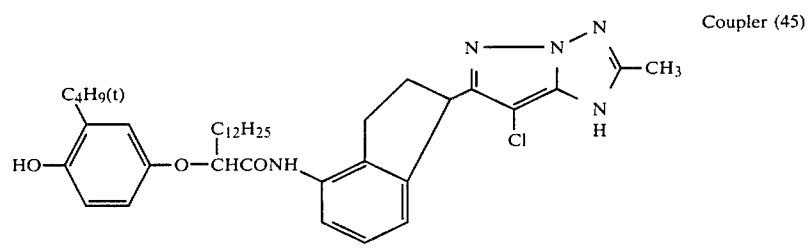
Coupler (45)

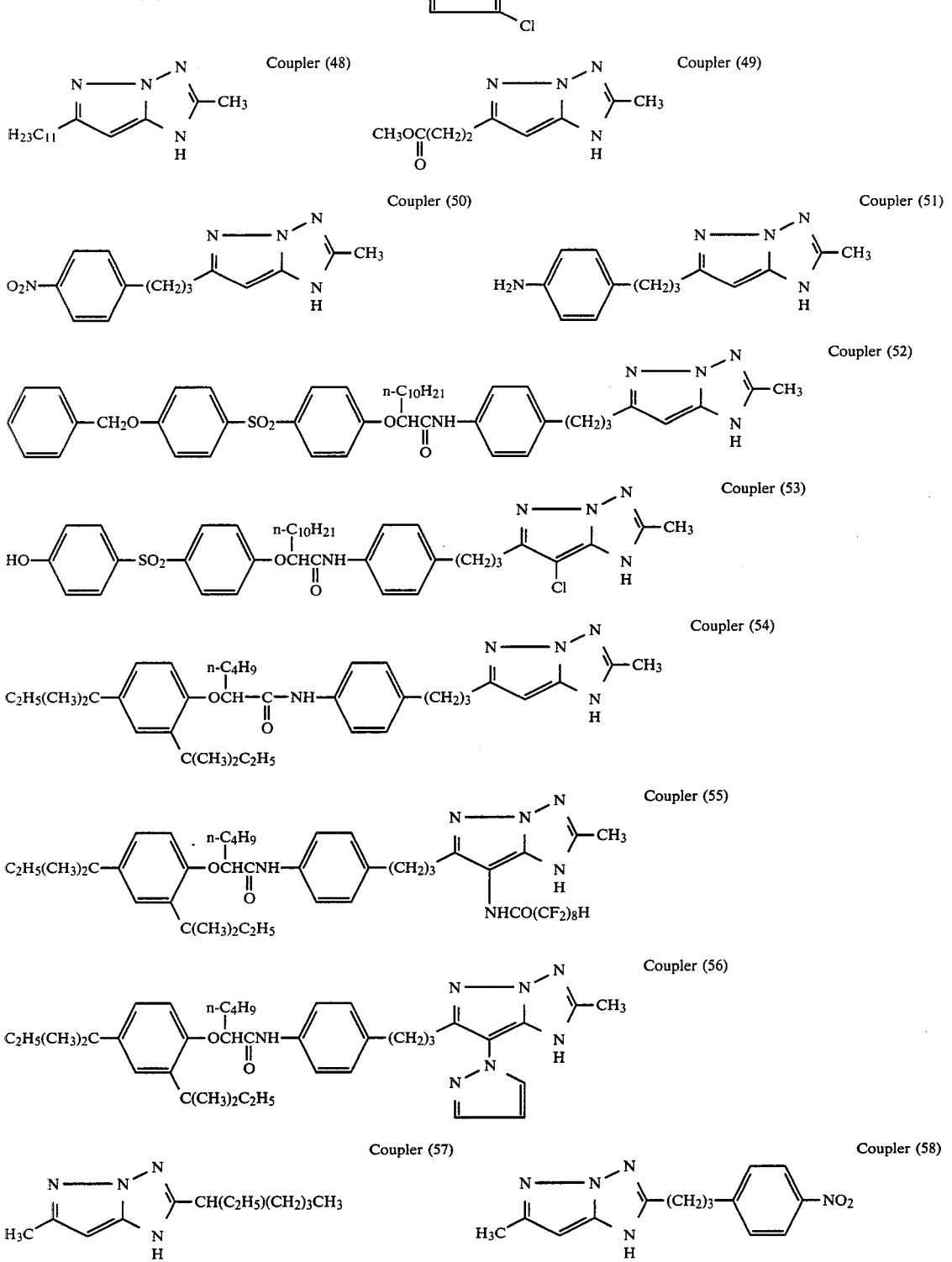

-continued
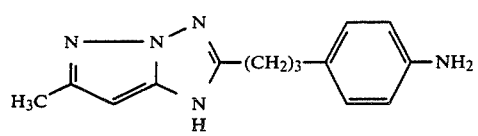
Coupler (59)
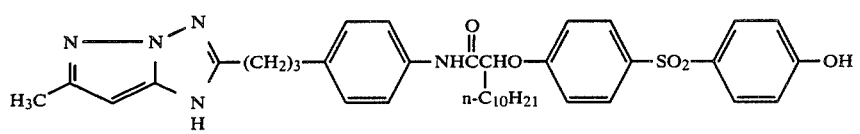
Coupler (60)
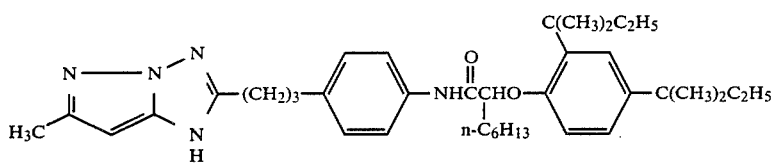
Coupler (61)
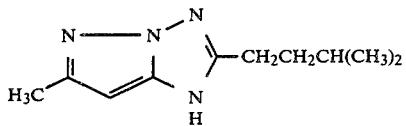
Coupler (62)
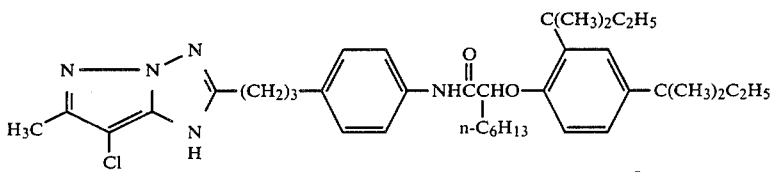
Coupler (63)
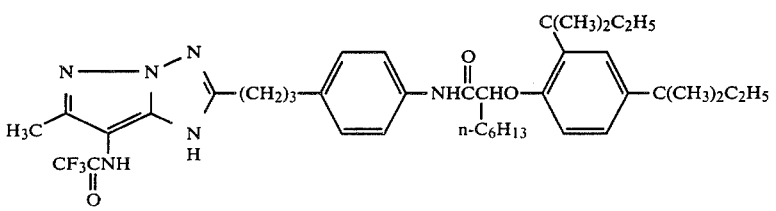
Coupler (64)
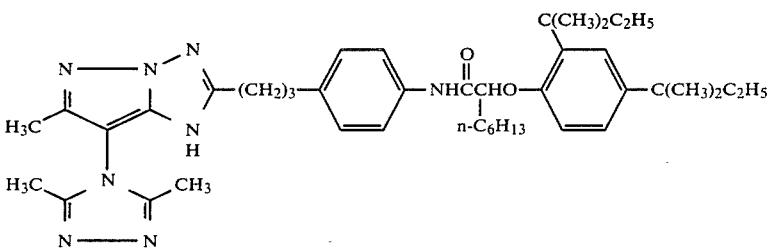
Coupler (65)
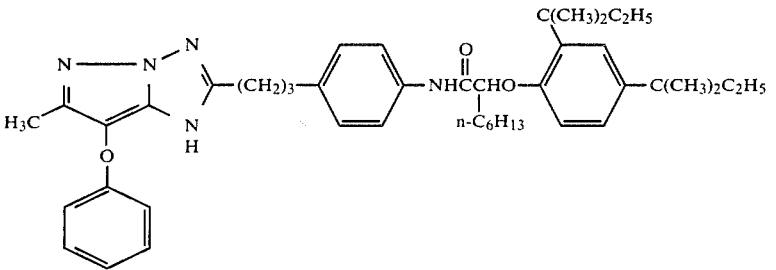
Coupler (66)

-continued
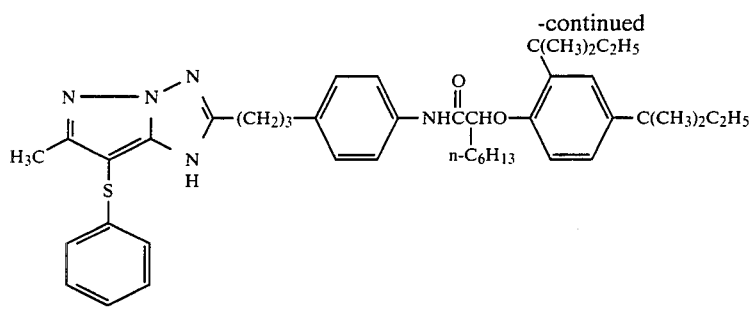
Coupler (67)
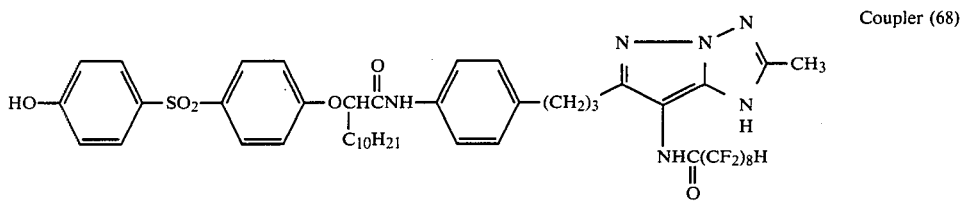
Coupler (68)
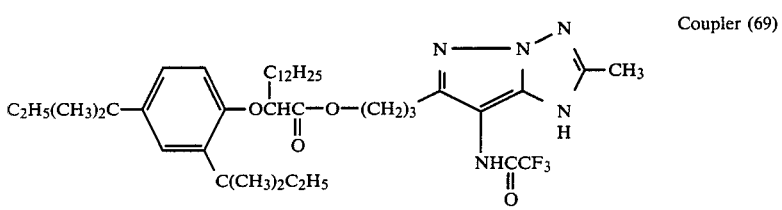
Coupler (69)
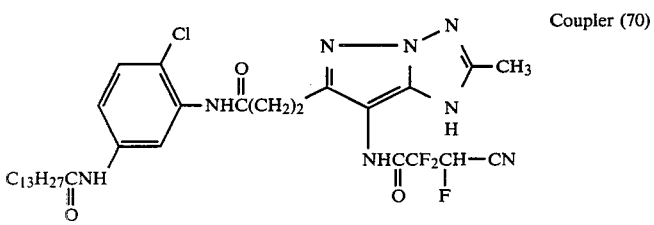
Coupler (70)
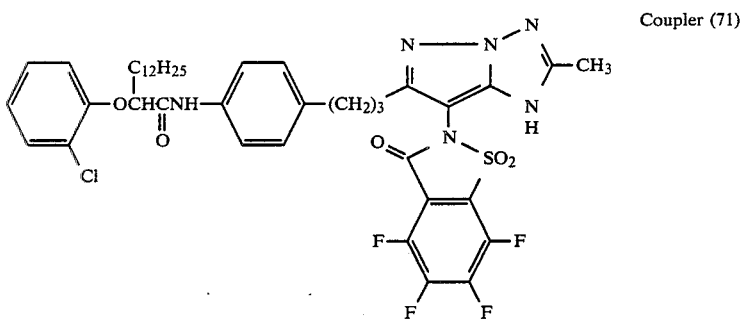
Coupler (71)
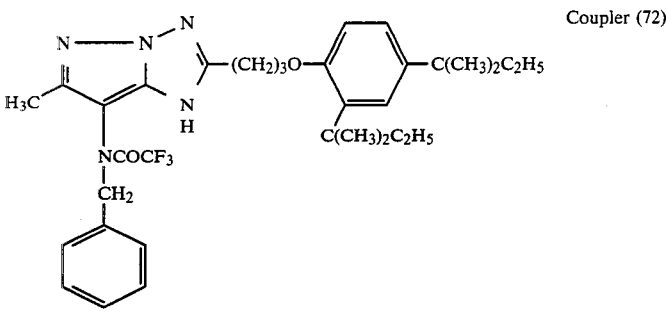
Coupler (72)
The magenta color forming couplers according to the present invention can be generally synthesized using any of six methods, reaction schemes of which are shown below.

Method I

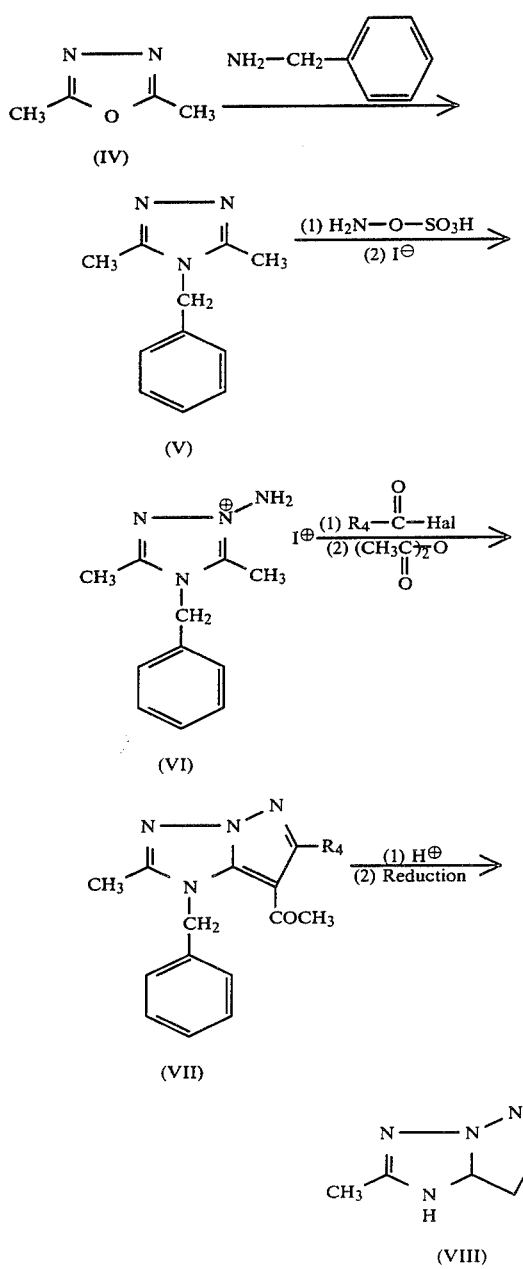

In the above formulae, $R_4$ represents an alkyl group, an aryl group or heterocyclic group; and Hal represents a halogen atom.

The starting material of the formula (IV) can be synthesized by the method as described in Ber., Vol. 32, page 797 (1899).

Method II

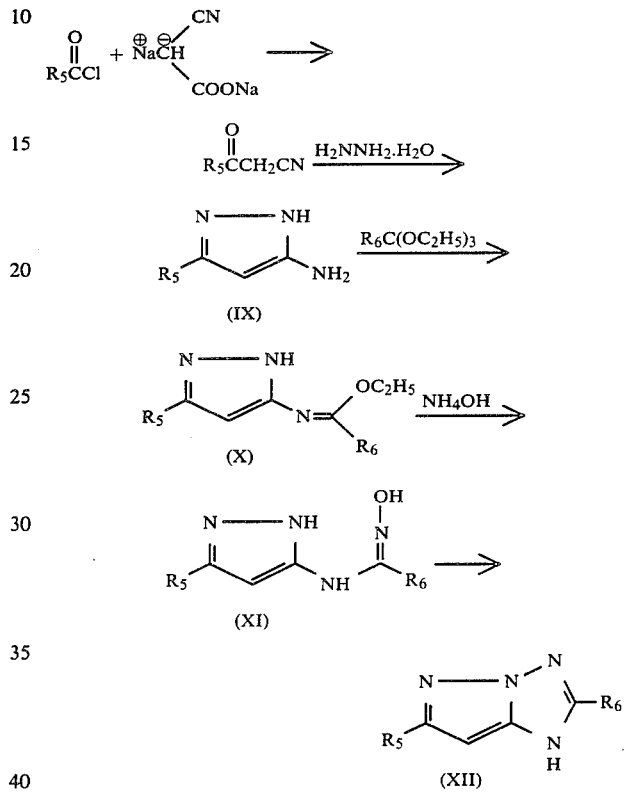

The target compound in the structural formula of which $R_5$ and $R_6$ independently represent an alkyl group, an aryl group, or a heterocyclic group can be synthesized by following the scheme indicated above. Either of the groups, $R_5$ and $R_6$, may be substituted. Specifically, where $R_5$ is methyl, the compound of (IX) can be readily obtained by reaction of 3-aminocrotonitrile with hydrazine. This method is characterized by producing the target compound by subjecting the reaction mixture to dehydrating cyclization condensation in the final stage of reaction.

Method III

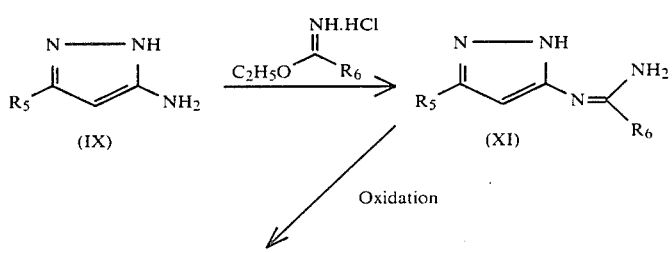

Method III

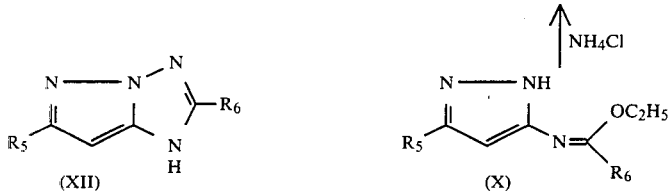

This method comprises obtaining the compound (XII) of this invention by subjecting to oxidative condensation the compound (XI) derived from either the intermediate of the Method II, i.e., 5-amino-3-substituted-pyrazole (IX), or the immediately ensuing intermediate (X). In the structural formulae of the compounds involved in this method, $R_5$ and $R_6$ independently represent an alkyl group, an aryl group, or a heterocyclic group. Either of the groups, $R_5$ and $R_6$, may be substituted.

METHOD IV

This method involves the synthesis of a pyrazolotriazole of this invention having an amino group at the 6-position from 3,5-diaminopyrazole as the starting material by subjecting this starting material to dehydrating cyclization condensation by the procedure of the second method while keeping the amino group at the 3-position protected. A typical reaction scheme for this method is as follows.

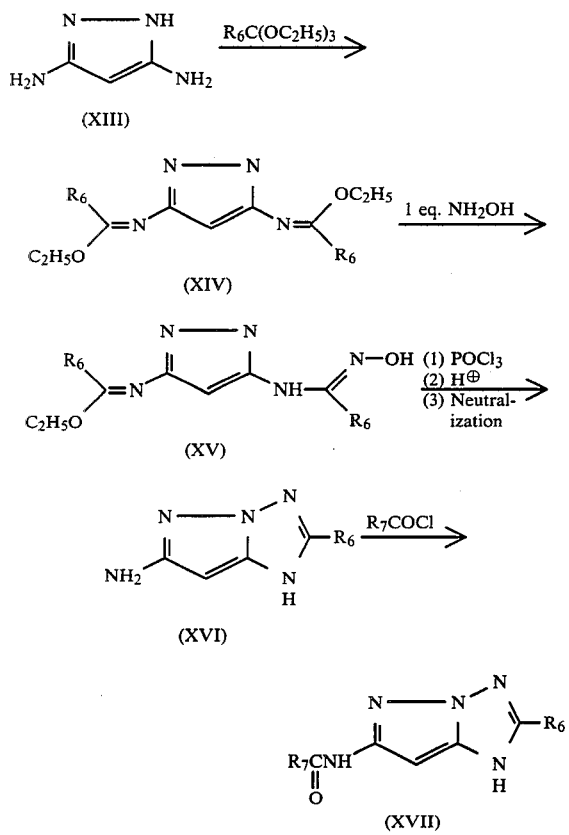

In the structural formulae indicated above, $R_6$ represents an alkyl, aryl, or heterocyclic group and $R_7$ represents an alkyl, aryl, heterocyclic, alkoxy, aryloxy, alkylamino, or arylamino group. $R_7SO_2Cl$ may be used in the place of $R_7COCl$. The aforementioned starting material (XIII) can be synthesized by the method disclosed in J. Prakt. Chem., Vol. 320, page 533 (1978).

Method V

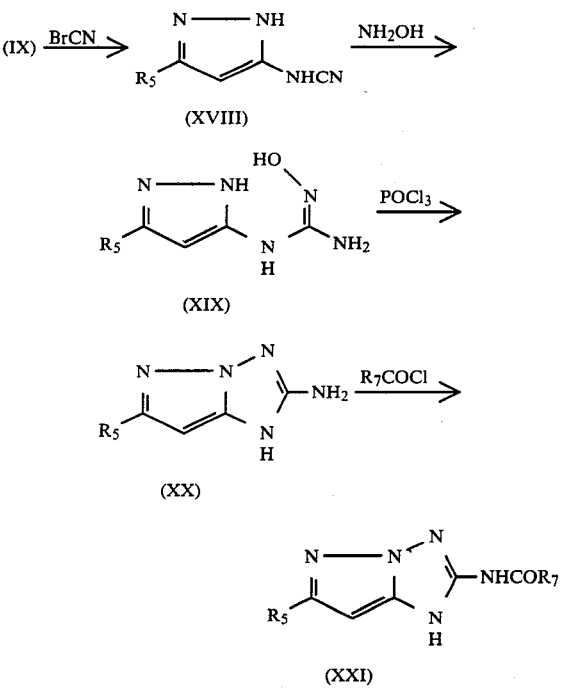

In the structural formulae indicated above, $R_5$ and $R_7$ independently represent any of the substituents indicated with respect to the structural formulae involved in the Method II and Method IV.

METHOD VI

Synthesis methods of polymer couplers are generally described below.

Polymer couplers can be synthesized by solution polymerization and emulsion polymerization. With respect to the solution polymerization the methods as described in U.S. Pat. No. 3,451,820 and Japanese Patent Application (OPI) No. 28745/83 can be utilized (the term "OPI" as used herein refers to a "published unexamined Japanese patent application"). More specifically, a monomer coupler containing a part represented by the general formula (I) and a non-color-forming ethylenic monomer (for example, an acrylic acid such as acrylic acid, α-chloroacrylic acid, methacrylic acid, etc.; and an ester or an amide derived from an acrylic acid such as acrylamine, n-butylacrylamide, n-butyl methacrylate, methyl methacrylate, ethyl methacrylate, etc.) are dissolved in or mixed with a soluble organic solvent (for example, dioxane, methyl cellosolve, etc.) in an appropriate ratio and polymerization is initiated at an appropriate temperature (in a range from about 30° to 100° C.) with a free radical which is formed by a physical action such as irradiation of ultraviolet rays, high energy radiations, etc., or a chemical action of an initiator such as a persulfate, hydrogen peroxide, benzoyl peroxide, an azobisalkyronitrile, etc. The polymer thus-synthesized is isolated by extraction with an organic solvent, concentration or pouring into water after the completion of the polymerization reaction. With respect to emulsion polymerization the method as described in U.S. Pat. No. 3,370,952 can be utilized.

General methods for introducing a group capable of being released upon coupling into a coupler are described in the following.

(1) METHOD FOR CONNECTING OXYGEN ATOM

A 4-equivalent mother coupler according to the present invention, i.e., pyrazolo[1,5-b]-1,2,4-triazole type coupler, is converted to a dye according to the method as described in Example 1 hereinafter. The resulting dye is hydrolyzed in the presence of an acid catalyst to form a ketone body thereof. The ketone body is hydrogenated with a Pd-carbon catalyst, or reduced with Zn-acetic acid or with sodium borohydride to produce a 7-hydroxy-pyrazolo[1,5-b]-1,2,4-triazole. The resulting triazole is reacted with one of various kinds of halides to obtain the desired coupler which has an oxygen atom as the connecting atom to the coupling releasing group. For more detail the descriptions in U.S. Pat. No. 3,926,631 and Japanese Patent Application (OPI) No. 70817/82 can be referred to.

(2) METHOD FOR CONNECTING NITROGEN ATOM

Methods for connecting a nitrogen atom are broadly classified into three groups. A method belonging to the first group comprises introducing a nitroso group to the coupling active position of a coupler using an appropriate nitrosating agent, reducing the nitroso group by an appropriate method (for example, a hydrogenation method using Pd-carbon, etc., as a catalyst, a chemical reduction method using stannous chloride, etc., or so on) to convert to 7-amino-pyrazolo[1,5-b]-1,2,4-triazole, and reacting the resulting amino compound with one of various kinds of halide, as described in U.S. Pat. No. 3,419,391. According to this method, amido compounds are mainly synthesized.

A method belonging to the second group comprises halogenating the 7-position of a coupler using an appropriate halogenating agent, for example, sulfuryl chloride, chlorine gas, bromine, N-chlorosuccinimide, N-bromosuccinimide, etc., as described in U.S. Pat. No. 3,725,067, and then replacing the resulting halogen atom by a nitrogen-containing hetero ring in the presence of an appropriate base catalyst, for example, triethylamine, sodium hydroxide, diazabicyclo-[2,2,2]-octane, anhydrous potassium carbonate, etc., as described in Japanese Patent Publication No. 45135/81 to synthesize a coupler having a coupling releasing group connecting through a nitrogen atom at the 7-position thereof. According to this method couplers having a phenoxy group at the 7-position thereof which are compounds connecting through an oxygen atom can also be synthesized.

A method belonging to the third group is effective for the introduction of an aromatic nitrogen-containing hetero ring of 6π- or 10π-electron system to the 7-position of a coupler. This method comprises adding two or more moles of an aromatic nitrogen-containing hetero ring of 6π- or 10π-electron system to 1 mole of a 7-halogenated compound as prepared using the method described in the above second group and heating the resulting mixture at a temperature ranging from 50° C. to 150° C. in the absence of a solvent or at a temperature ranging from 30° C. to 150° C. in the presence of an aprotic polar solvent such as dimethylformamide, sulfolane, hexamethylphosphotriamide, etc., to introduce an aromatic nitrogen-containing heterocyclic group to the 7-position wherein the heterocyclic group is connected through the nitrogen atom as described in Japanese Patent Publication No. 36577/82.

(3) METHOD FOR CONNECTING SULFUR ATOM

A coupler having an aromatic mercapto group or a heterocyclic mercapto group at the 7-position thereof can be synthesized using the method as described in U.S. Pat. No. 3,227,554. More specifically, an aryl mercaptan, a heterocyclic mercaptan or a corresponding disulfide is dissolved in a halogenated hydrocarbon type solvent, converted into sulfenyl chloride using chlorine or sulfuryl chloride and added to an aprotic solvent containing a 4-equivalent pyrazolo[1,5-b]-1,2,4-triazole type coupler dissolved therein whereby the desired compound can be synthesized. In order to introduce an alkylmercapto group into the 7-position, a method wherein a mercapto group is introduced into the coupling active position of a coupler and the mercapto group is reacted with a halide to synthesize a 7-alkylthio compound and a method wherein a 7-alkylthio compound is synthesized in one step using an S-(alkylthio)isothiourea hydrochloride (or hydrobromide) as described in U.S. Pat. No. 4,264,723 are useful.

(4) METHOD FOR CONNECTING CARBON ATOM

A coupler releasing a diarylmethane series compound can be synthesized by the method as described in Japanese Patent Publication No. 34937/77, and an aldehyde-bis type coupler can be synthesized by the methods as described in Japanese Patent Application (OPI) Nos. 105820/76, 129035/78 and 48540/79.

Specific examples of synthesizing the magenta coupler according to the present invention are set forth below.

SYNTHESIS EXAMPLE 1

Synthesis of 1H-2,6-dimethylpyrazolo[1,5-b]-1,2,4-triazole [Coupler (1)]

2,5-Dimethyl-1,3,4-oxadiazole obtained by thermal decomposition of tetraacetyl hydrazine was reacted with benzylamine at 110° C. for 4 hours to synthesize 4-benzyl-3,5-dimethyl-1,2,4-triazole in a yield of 73%.

Melting Point: 125° to 127° C.

75 g of the triazole thus-synthesized was reacted with an aqueous solution of potassium hydroxylamine-O-sulfonate obtained from 66 g of hydroxylamine-O-sulfonic acid and 40 g of potassium hydroxide at 80° to 90° C. for 6 hours. After cooling to room temperature, the pH of the reaction mixture was adjusted to between 8 and 9 using a 50% aqueous solution of potassium carbonate. The potassium sulfate formed was removed by filtration and the filtrate was extracted three times with chloroform. From the chloroform extract 44 g (50% yield) of the triazole which was the starting material was recovered. To the aqueous layer was added a 57% aqueous solution of hydroiodic acid to adjust the pH thereof to 3 under cooling with ice whereby crystals were deposited. The crystals were collected by filtration and recrystallized from ethanol at −20° C. to obtain 39 g (31% yield) of N-aminotriazonium iodide as light yellow crystals.

Melting Point: 180° to 181° C.

Nuclear Magnetic Resonance Spectrum (CDCl$_3$+DMSO-d$_6$): 2.39 (3H, s), 2.67 (3H, brs), 5.35 (2H, s), 6.66 (1H, —NH), 7.0–7.2 (2H), 7.2–7.46 (4H, —NH included).

8 g of the N-aminotriazonium iodide thus-obtained was dissolved in 50 ml of DMF, to the solution was added 40 ml of acetic anhydride and the mixture was heated to 120° C. Then, 12.5 g of sodium acetate was added and the mixture was stirred at 120° to 130° C. for 4 hours. After removing the DMF and acetic anhydride using an evaporator, the reaction mixture was rendered alkaline with a saturated aqueous sodium carbonate solution and extracted with chloroform. The extract was dried over anhydrous magnesium sulfate and the solvent was removed to obtain a brown oily product. The oily product was purified using a silica gel column with a solvent system of n-hexane and ethyl acetate to obtain 2 g (30% yield) of 7-acetyl-1-benzyl-2,6-dimethylpyrazolo[1,5-b]-1,2,4-triazole.

Melting Point: 105° to 107° C.

Nuclear Magnetic Resonance Spectrum (CDCl$_3$): 2.36 (3H, s), 2.43 (3H, s), 2.60 (3H, s), 5.80 (2H, s), 7.0–7.2 (2H), 7.2–7.36 (3H).

2 g of the 7-acetyl-1-benzyl-2,6-dimethylpyrazolo[1,5-b]-1,2,4-triazole thus-obtained was dissolved in 20 ml of ethanol, to the solution was added 20 ml of concentrated hydrochloric acid and the mixture was refluxed by heating. After about 6 hours, the ethanol was distilled off under reduced pressure, the reaction mixture was rendered alkaline with a saturated aqueous solution of sodium hydrogencarbonate and extracted with ethyl acetate to obtain 1.6 g (95% yield) of almost pure deacetylated compound, i.e., 1-benzyl-2,6-dimethylpyrazolo[1,5-b]-1,2,4-triazole.

Melting Point: 87° to 88° C.

Nuclear Magnetic Resonance Spectrum (CDCl$_3$): 2.32 (3H, s), 2.44 (3H, s), 5.02 (2H, s), 5.22 (1H, s), 7.10–7.40 (5H).

1.6 g of the 1-benzyl-2,6-dimethylpyrazolo-[1,5-b]-1,2,4-triazole thus-obtained was reacted with about 0.8 g of metallic sodium in liquid ammonia to obtain 0.67 g (70% yield) of the desired coupler, i.e., 1H-2,6-dimethylpyrazolo[1,5-b]-1,2,4-triazole as colorless crystals.

Melting Point: 274° to 275° C. (decomposed).

Mass Spectrometry: 136 (M+, 100%).

Elemental Analysis: Calculated (%): C: 52.93, H: 5.92, N: 41.15 Found (%): C: 52.85, H: 6.02, N: 41.01.

Nuclear Magnetic Resonance Spectrum (CDCl$_3$: pyridine-d$_5$=1:1) 2.35 (3H, s), 2.43 (3H, s), 5.50 (1H, s).

SYNTHESIS EXAMPLE 2

Synthesis of Coupler (5)

To a DMF solution of the N-aminotriazonium iodide as described in SYNTHESIS EXAMPLE 1 was added 1 equivalent of 4-(3-pentadecylphenoxy)butyryl chloride and the mixture was gradually heated from room temperature to 120° C. Then, 6 equivalents of sodium acetate and an excess amount of acetic anhydride were added to the mixture which was heated at between 120° C. and 130° C. for about 6 hours. The same procedure and purification as described in SYNTHESIS EXAMPLE 1 were conducted to obtain 7-acetyl-1-benzyl-2-methyl-6-(3-pentadecylphenoxy)propylpyrazolo-[1,5-b]-1,2,4-triazole in a yield of about 30%. Using the compound, 6-(3-pentadecylphenoxy)propylpyrazolo-[1,5-b]-1,2,4-triazole was synthesized in the same manner as described in SYNTHESIS EXAMPLE 1.

SYNTHESIS EXAMPLE 3

Coupler (1) was synthesized using Method II as follows.

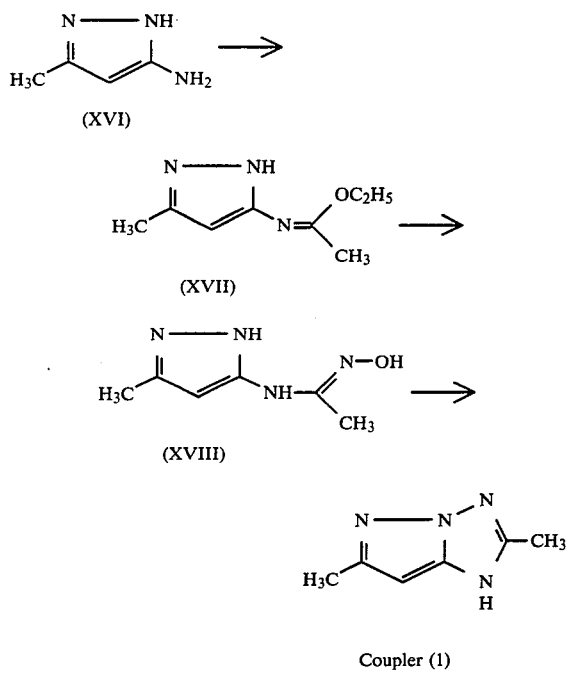

Coupler (1)

2.4 g (25 mmol) of 5-amino-3-methylpyrazole (XVI) obtained by reaction of 3-aminocrotonitrile with hydrazine hydrate, and 6.0 g (37 mmol) of triethyl orthoacetate were added to 20 ml of toluene and the resulting mixture was refluxed with heating for about 10 hours. The resultant reaction mixture was then distilled to remove the toluene. Consequently, a crude product of (XVII) was obtained in an oily state.

Nuclear Magnetic Resonance Spectrum (CDCl$_3$): 1.28 (3H, 6, J=7.5), 1.96 (3H, s), 2.22 (3H, s), 4.19 (2H, q, J=7.5), and 5.50 (1H, s).

A solution of 2.6 g (37 mmol) of hydroxylamine hydrochloride in 20 ml of methanol was combined with 7.4 ml of a 28% sodium methoxide solution in methanol at 0° C. The resultant mixture was filtered to separate the precipitated sodium chloride. The filtrate was immediately added at 0° C. to a solution of (XVII), obtained as described above, in methanol. At the end of this addition, the resultant mixture was allowed to warm up spontaneously to room temperature, stirred for about 1 hour, and distilled in vacuo to remove the methanol. By washing the resulting crystals with chloroform, 3.2 g (83% in yield) of (XVIII) was obtained.

Melting Point: 180° to 185° C. (decomposition).

Nuclear Magnetic Resonance Spectrum (DMSO-$d_6$): 1.87 (3H, s), 2.12 (3H, s), and 5.65 (1H, s).

Elemental Analysis: Calculated (%): C: 46.74, H: 6.54, N: 36.34, Found (%): C: 46.66, H: 6.63, N: 36.10.

In 150 ml of tetrahydrofuran (THF), 1.5 g (9.7 mmol) of (XVIII) produced as described above was dissolved. To the resultant solution, 1.2 g of triethylamine was added and then 2.2 g of p-toluenesulfonyl chloride was added incrementally at room temperature. Then, the resultant mixture was stirred for 30 minutes. The stirred mixture and 150 ml of THF further added thereto were refluxed with heating for 7 hours. The reaction mixture consequently formed was filtered to separate an amine salt formed therein as a precipitate. The filtrate was concentrated. By purifying the concentrate by chromatography, 0.9 g (68% in yield) of Coupler (1) was obtained. The physical constants determined for Coupler (1) were perfectly in agreement with those obtained in SYNTHESIS EXAMPLE 1. A small amount of Coupler (47) was obtained as a secondary product.

Melting Point: 250° to 255° C. (decomposition).

SYNTHESIS EXAMPLE 4

Coupler (48) was synthesized using Method I as follows.

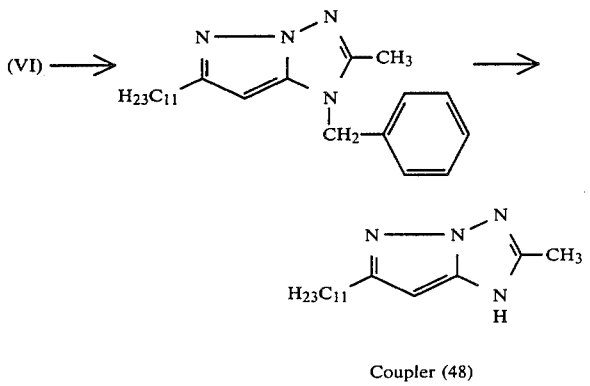

Coupler (48)

In 100 ml of DMF, 5 g (16 mmol) of N-aminotriazolium iodide (VI) described in SYNTHESIS EXAMPLE 1, 5 equivalents, 30 g (79 mmol), of lauric anhydride, and 11 g (77 mmol) of tri-n-propylamine were heated at 140° C. to 150° C. for about 10 hours. The resultant reaction mixture was vacuum-distilled to remove the DMF. The residue after evaporation was combined with ethyl acetate to precipitate unreacted lauric anhydride, which was separated by filtration. The filtrate was transferred into a separatory funnel and thoroughly shaken with a 2N sodium hydroxide aqueous solution to effect phase separation. The aqueous layer was extracted twice with ethyl acetate. The ethyl acetate layer was washed with a saturated aqueous solution of sodium chloride and then dried over magnesium sulfate. The residue consequently obtained and 30 ml of concentrated hydrochloric acid and 50 ml of ethanol added thereto were refluxed with heating for about 4 hours, then the ethanol removed, and extracted with ethyl acetate. The extract was subjected to conventional work up procedure and purified using a silica gel column. Consequently, 0.8 g (14% in yield) of 1-benzyl derivative was obtained.

Nuclear Magnetic Resonance Spectrum (CDCl$_3$): 0.88 (3H, br t, J=~7), 1.30 (20H, br s), 2.40 (3H, s), 2.60 (2H, t, J=7.5), 5.03 (2H, s), 5.25 (1H, s), and 7.10–7.45 (5H).

By debenzylation of the 1-benzyl derivative with sodium in liquid ammonia, Coupler (48) sparingly soluble in organic solvents except for alcohols was obtained in a yield of about 90%.

Melting Point: 154° to 155° C.

SYNTHESIS EXAMPLE 5

Coupler (6) was synthesized from intermediate (VI) using Method I as follows:

In 8 ml of anhydrous DMF, 1.0 g (3.16 mmol) of (VI) was dissolved. The resultant solution and 3.6 g (15.8 mmol) of benzoic anhydride and 2.3 g (15.8 mmol) of tri-n-propylamine added thereto were stirred at 130° C. for 24 hours. The resultant reaction mixture was distilled under vacuum to remove DMF and tri-n-propylamine. The residue after distillation and 30 ml of ethanol and 10 ml of concentrated hydrochloric acid added thereto were refluxed with heating for 5 days. The resultant reaction mixture was subjected to vacuum distillation to remove the ethanol and concentrated hydrochloric acid. The residue after the distillation was extracted with ethyl acetate. The extract was dried, concentrated, and purified by silica gel chromatography. Consequently, 0.2 g (22% in yield) of the 1-benzyl derivative was obtained.

Nuclear Magnetic Resonance Spectrum (CDCl$_3$): 2.35 (3H, s), 4.95 (2H, s), 5.65 (1H, s), 7.05–7.50 (8H), and 7.80 (2H, dd, J=9.0, 1.5).

By reducing 0.2 g (0.69 mmol) of the 1-benzyl derivative with 0.05 g of sodium in liquid ammonia, 0.12 g (87% in yield) of the desired Coupler (6) was obtained.

Melting Point: about 190° C. (gradual decomposition).

SYNTHESIS EXAMPLE 6

Coupler (49) was synthesized by first synthesizing an N-benzyl derivative of Coupler (49) from intermediate (VI), using Method I and then removing the protective benzyl group from the N-benzyl derivative.

In 15 ml of N-methyl pyrrolidone, 1.00 g (32 mmol) of (VI) was stirred at room temperature. To the resultant solution, 2.93 g of methoxycarbonyl propionic anhydride and 4.8 ml of tri-n-propylamine were added in the order mentioned. The resultant mixture was heated over an oil bath at 130° C. for 3 hours. The resultant hot mixture was cooled, diluted with ethyl acetate, and washed twice each with 100 ml of cold water. The ethyl acetate layer was dried over anhydrous magnesium sulfate and then concentrated. The concentrate and 30 ml of methanol and 30 ml of concentrated hydrochloric acid added thereto were refluxed with heating for 7 hours. The hot refluxed product was cooled and then subjected to vacuum distillation to remove ethanol. The residue after the vacuum distillation was poured in 100 ml of ice water, neutralized to pH 7, and extracted three times each with 50 ml of ethyl acetate. The ethyl acetate layer was dried over anhydrous magnesium sulfate, concentrated, and purified with a silica gel column (20 g). Consequently, 0.16 g (17% in yield) of an N-benzyl derivative of Coupler (49) was obtained in an oily state.

Nuclear Magnetic Resonance Spectrum (CDCl$_3$): 2.42 (3H, s), 2.60-3.15 (4H, m), 3.63 (3H, s), 5.02 (2H, s), 5.26 (1H, s), and 7.12-7.50 (5H, m).

By reducing this N-benzyl derivative with sodium by the procedure described above, Coupler (49) was obtained in a yield of about 80%.

Melting Point: 120° to 122° C.

SYNTHESIS EXAMPLE 7

Couplers (51), (52), (9) and (53) were synthesized from intermediate (VI) using Method I as follows:

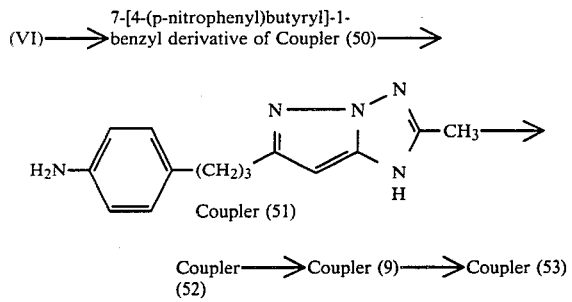

In 150 ml of DMF were dissolved 9.5 g (30 mmol) of (VI), 65 g (150 mmol) of 4-(p-nitrophenyl)butyric anhydride, and 57 ml (300 mmol) of tri-n-propylamine. The resultant mixture was stirred and heated for 4 hours over an oil bath at 130° C., then for 2 hours over an oil bath at 140° C., and further for 6 hours over an oil bath at 160° C. The resultant reaction mixture was subjected to vacuum distillation to remove DMF. The residue after the distillation was dissolved in ethyl acetate. The ethyl acetate solution was washed twice with a 2N NaOH aqueous solution. The ethyl acetate layer was dried over anhydrous magnesium sulfate, then concentrated, and subjected to silica gel column chromatography (using 600 g of silica gel and an eluant formed by mixing hexane with ethyl acetate at 2:1 to 1:1 by volume). Consequently, 7.6 g (45% in yield) of the 7-[4-(p-nitrophenyl)butyryl]-1-benzyl derivative of Coupler (50) was obtained.

Nuclear Magnetic Resonance Spectrum (CDCl$_3$): 2.40 (3H, s), 1.8-3.3 (12H, m), ~5.80 (2H, s), 7.0-7.4 (9H, m), and 8.1 (4H, m).

In a mixed solvent of 150 ml of EtOH and 50 ml of concentrated hydrochloric acid, 7.6 g (13 mmol) of the 7-[4-(p-nitrophenyl)butyryl]-1-benzyl derivative of Coupler (50) was refluxed with heating for 10 hours. The resultant reaction mixture was combined with 100 ml of water and subjected to vacuum concentration to remove the ethanol. The residue after the vacuum concentration was neutralized with aqueous ammonia and extracted with ethyl acetate. The ethyl acetate layer was dried over anhydrous magnesium sulfate, concentrated, and subjected to silica gel column chromatography (using 140 g of silica gel and an eluant formed by mixing hexane with ethyl acetate at a ratio of 1:1 by volume). Consequently, 3.8 g (76% in yield) of the N-benzyl derivative of Coupler (50) was obtained.

Nuclear Magnetic Resonance Spectrum (CDCl$_3$): 2.03 (2H, m), 2.44 (3H, s), 2.58-2.85 (4H, m), 5.02 (2H, s), 5.20 (1H, s), 7.04-7.40 (7H, m), and 8.04 (2H, d, J=8.0).

In 80 ml of isopropyl alcohol, 18 g (0.32 mmol) of reduced iron, 1.3 g (25 mmol) of ammonium chloride, and 8 ml of cold water were vigorously stirred and heated until refluxing was achieved. The resultant reaction mixture and 0.2 ml of concentrated hydrochloric acid added thereto were refluxed with heating for 30 minutes. To the refluxed mixture, 18.0 g (47.9 mmol) of the aforementioned 6-[3-(p-nitrophenyl)propyl]-1-benzyl derivative of Coupler (50) was added incrementally over a period of 20 minutes. The resultant mixture was refluxed with heating for 1 hour. The reaction mixture was filtered through celite. The celite was thoroughly washed with ethanol. The filtrate was concentrated, dissolved in ethyl acetate, washed with cold water, and then dried over anhydrous magnesium sulfate. By concentrating the resultant product, 15.8 g (95% in yield) of the 1-benzyl derivative of Coupler (51) was obtained.

Nuclear Magnetic Resonance Spectrum (CDCl$_3$): 1.95 (2H, m), 2.38 (3H, s), 2.40-2.76 (4H, m), 3.36 (2H, br), 4.97 (2H, s), 5.20 (1H, s), 6.53 (2H, m), 5.91 (2H, m), and 7.00-7.38 (5H, m).

The 1-benzyl derivative of Coupler (51) in the amount of 15.8 g (45.7 mmol) was added to 200 ml of liquid ammonia in a refluxing state and the resulting mixture was stirred. To the resultant mixture, 2.6 g (0.11 mol) of metallic solium was added incrementally. Then ammonium chloride was added thereto incrementally. The resulting mixture was allowed to stand overnight to remove ammonia. The residue was dissolved in a 2N HCl aqueous solution and washed with ethyl acetate. The aqueous layer was neutralized with aqueous ammonia and then filtered to separate the precipitate consequently formed therein. The precipitate was washed first with cold water and then with acetonitrile and thereafter dried. Consequently, 7.9 g (68% in yield) of Coupler (51) was obtained in a substantially pure state.

Nuclear Magnetic Resonance Spectrum (CDCl$_3$+DMSO-d$_6$): 1.88 (2H, br, quintet, J=~7), 2.41 (3H, s), 2.3-2.8 (4H), 5.42 (1H, s), 6.56 (2H, d, J=8.5), and 6.90 (2H, d, J=8.5).

Coupler (51) in the amount of 3.00 g (11.7 mmol) was mixed first with 50 ml of acetonitrile and then with 25 ml of N,N-dimethylacetamide and the resultant mixture was stirred and heated until refluxing was achieved. To the mixture, a solution of 7.19 g (12.9 mmol) of the acid chloride

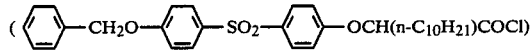

in 20 ml of acetonitrile was added dropwise over a 20 minute period. The resultant mixture was further refluxed for 20 minutes. Then, with a solution of 0.72 g (0.13 mmol) of the same acid chloride in 10 ml of acetamide added dropwise thereto over a 10 minute period, the reaction mixture was further refluxed for 30 minutes. The hot mixture resulting from the refluxing was cooled, poured in 500 ml of cold water, and extracted with ethyl acetate. The ethyl acetate layer was dried over anhydrous magnesium sulfate, concentrated, and subjected to silica gel column chromatography (using 300 g of silica gel and an eluate obtained by mixing chloroform with methanol at a ratio of 60:1 by volume). Consequently, 7.25 g (80% in yield) of Coupler (52) was obtained in a solid state.

Elemental Analysis: Calculated (%): C: 69.65, H: 6.88, N: 9.02, S: 4.13, Found (%): C: 68.99, H: 6.90, N: 8.90, S: 4.07.

Mass Analysis (FD): 776 M+, b.p.).

Nuclear Magnetic Resonance Spectrum (CDCl$_3$): 0.86 (3H, br t, J=7), 1.0–2.2 (20H, m), 2.38 (3H, s), 2.5–2.8 (4H, m), 4.68 (1H, br t, J=6), 5.05 (2H, s), 5.45 (1H, s), 6.9–7.4 (13H, m), 7.7–7.9 (4H, m), 8.17 (1H, s), and 11.6 (1H, br).

A solution of 3.3 g (4.3 mmol) of the 6-[3-(p-nitrophenyl)-propyl]-1-benzyl derivative of Coupler (50) in 60 ml of THF was combined with 0.66 g of 10% Pd/C. The resultant mixture was stirred at 60° C. under a hydrogen pressure of 60 atmospheres for 3 hours. The stirred mixture was cooled and filtered to separate the catalyst. The filtrate was concentrated. By subjecting the concentrated filtrate to silica gel column chromatography (using 90 g of silica gel and an eluant obtained by mixing chloroform with methanol at a ratio of 1:0 to 30:1 by volume), 2.7 g (92% in yield) of Coupler (9) in a solid state was obtained.

Mass Analysis (FD): 687 (M++2, 50%), 686 (M++1,100), 685 (M+, 30).

In 100 ml of dichloromethane, 4.25 g (6.20 mmol) of Coupler (9) and 50 ml of THF were stirred at room temperature to effect solution. The resultant solution and 795 mg (5.95 mmol) of N-chloro-succinimide added thereto were stirred at room temperature for 15 minutes. The resultant mixture was washed twice each with 150 ml of cold water, and then dried over anhydrous magnesium sulfate. The resultant mixture was concentrated and then subjected to silica gel column chromatography (using 700 g of silica gel and an eluant formed by mixing chloroform with methanol in a ratio of 50:1 to 30:1 by volume). Consequently, 4.04 g (90% in yield) of Coupler (53) in a solid state was obtained.

Mass Analysis (FD): 722, 721, and 720 (9:7:9), 220 (b.p.).

SYNTHESIS EXAMPLE 8

Coupler (17) was synthesized through the Coupler (54) from Coupler (51) as the starting material.

In 30 ml of acetonitrile, 1.79 g (7.00 mmol) of Coupler (51) and 5 ml of N,N-dimethylacetamide were stirred under application of heat until the resultant mixture was refluxed. To the resultant mixture, a solution of 2.83 g (7.70 mmol) of the acid chloride, [(t-C$_5$H$_{11}$)$_2$C$_6$H$_3$OCH(n-C$_4$H$_9$)COCl], in 10 ml of acetonitrile was added dropwise over a 15 minute period. The resultant mixture was further refluxed for 30 minutes. The resultant hot mixture was cooled, poured into 300 ml of cold water, and extracted using ethyl acetate. The ethyl acetate layer was dried over anhydrous magnesium sulfate, then concentrated, and subjected to silica gel column chromatography (using 100 g of silica gel and an eluant obtained by mixing chloroform with methanol in a ratio of 70:1 by volume). Consequently, 3.12 g (76% in yield) of Coupler (54) in a solid state was obtained.

Elemental Analysis: Calculated (%): C: 73.81, H: 8.77, N: 11.95, Found (%): C: 73.64, H: 8.95, N: 11.93.

Nuclear Magnetic Resonance Spectrum (CDCl$_3$): 0.50–1.00 (7H, m), 1.00–2.16 (26H, m), 2.44 (3H, s), 2.46–2.80 (4H, m), 4.66 (1H, t, J=6.0), 5.44 (1H, s), 6.90–7.34 (6H, m), and 7.64 (1H, d, J=9.0).

In 100 ml of dichloromethane, 3.10 g (5.29 mmol) of Coupler (54) and 50 ml of THF were stirred at room temperature to effect solution. The resultant solution and 706 mg (5.29 mmol) of N-chloro-succinimide added thereto were stirred for 10 minutes. The resultant mixture was washed twice each with 150 ml of cold water, and then dried over anhydrous magnesium sulfate. The reaction mixture was concentrated, crystallized by addition of acetonitrile, and refluxed with heating once. The resulting reaction mixture was cooled, separated off by filtration, washed with acetonitrile, and then dried. Consequently, 2.4 g (73% in yield) of Coupler (17) in a solid state was obtained.

Elemental Analysis: Calculated (%): C: 69.71, H: 8.12, N: 11.29, Cl: 5.72, Found (%): C: 69.36, H: 8.21, N: 11.25, Cl: 5.78.

Nuclear Magnetic Resonance Spectrum (CDCl$_3$): 0.48–1.00 (7H, m), 1.06–2.18 (26H, m), 2.45 (3H, s), 2.48–2.82 (4H, m), 4.67 (1H, t, J=6.0), 6.65 (1H, d, J=8.5), 6.91–7.34 (6H, m), and 7.87 (1H, s).

SYNTHESIS EXAMPLE 9

A fluorine-containing aliphatic carboxylic acid amide group was introduced as a coupling-off group in the 7-position of Coupler (54).

In 25 ml of acetic acid, 2.93 g (5.00 mmol) of Coupler (54) was stirred at room temperature. Into the resultant solution, 586 mg (5.00 mmol) of isoamyl nitrite was added dropwise. Then, the resultant mixture was stirred for one hour. The resultant mixture was gradually added to 300 ml of water. The reaction mixture was filtered to separate the precipitate. The separated precipitate was washed with cold water and dried under a vacuum. Consequently, 2.95 g (96% in yield) of a 7-nitroso derivative in a solid state was obtained.

In 50 ml of ethanol, 2.85 g (4.63 mmol) of the 7-nitroso derivative was heated under an atmosphere of nitrogen until the resultant mixture was refluxed. Into the resultant mixture, a solution of 4.38 g (23.1 mmol) of stannous chloride in 10 ml of concentrated hydrochloric acid was added dropwise over a period of 10 minutes. The resultant mixture was refluxed for 30 minutes and then cooled. The reaction mixture thus obtained was poured into 150 ml of cold water and extracted using ethyl acetate. The ethyl acetate layer was dried over anhydrous magnesium sulfate and then concentrated to dryness. The resultant dry mass was dissolved in 25 ml of pyridine and then cooled and stirred under a nitrogen atmosphere. To the stirred solution, 2.15 g (4.63 mmol) of the acid chloride, [H(CF$_2$)$_8$COCl], was added dropwise, with the stirring being continued for 1 hour. The resultant reaction mixture was poured into 250 ml of cold water and then extracted with ethyl acetate. The ethyl acetate layer was washed with 2N hydrochloric acid and then washed with cold water. The ethyl acetate layer was dried over anhydrous magnesium sulfate, then concentrated, and subjected to silica gel column chromatography (using 150 g of silica gel and an eluant obtained by mixing chloroform with methanol in a ratio of 100:1). By concentrating and drying the eluate, 3.43 g (72% in yield) of Coupler (55) was obtained.

Nuclear Magnetic Resonance Spectrum (CDCl$_3$): 0.52–1.01 (7H, m), 1.02–2.15 (26H, m), 2.42 (3H, s), 2.46–2.78 (4H, m), 4.60 (1H, t, J=6.0), 6.30 (1H, tt, J=51.0, 5.0), 4.5 (1H, d, J=8.5), 6.85–7.36 (6H, m), 8.90 (1H, brs), 10.0 (1H, brs), and 10.3 (1H, brs).

SYNTHESIS EXAMPLE 10

Coupler (62) was synthesized using Method II as follows. The final product was obtained from 5-amino-3-methyl pyrazole corresponding to (XII-A).

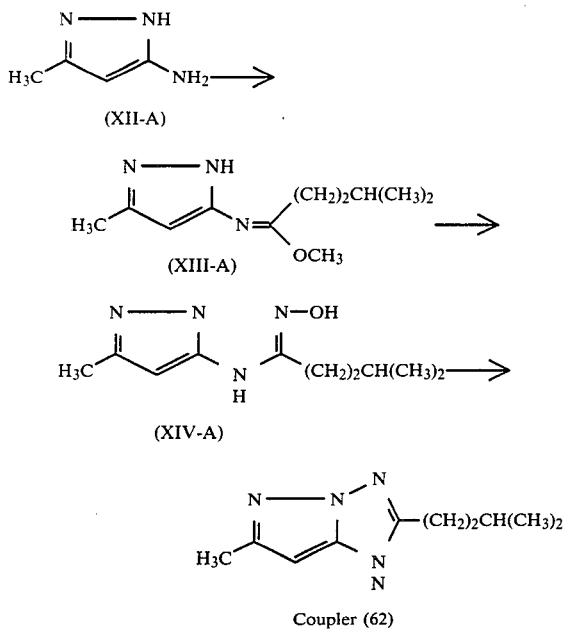

Coupler (62)

Trimethyl orthoisocaproate could be synthesized in a yield of about 50% from isocapronitrile via the imidate hydrochloride. Boiling point 75° to 77° C./28 mmHg.

In 200 ml of toluene, 19.8 g (0.11 mol) of the ortho ester and 10.9 g (0.11 mol) of (XII-A) were refluxed with heating for about 24 hours and thereafter subjected to vacuum distillation to remove the toluene. Consequently, a crude product of (XIII-A) in an oily state was obtained.

To this crude product was added at 0° C. a methanol solution of hydroxylamine prepared from 11.7 g (0.17 mol) of hydroxylamine hydrochloride and 34 ml of 28% sodium methoxide and then stirred at room temperature for 1 hour. The resultant reaction mixture was subjected to vacuum distillation to remove the methanol. The residue was combined with chloroform to precipitate fine crystals of (XIV-A). By filtering this mixture, 12 g (52% in yield) of crystals was obtained. The crystals were dissolved in 3 liters of tetrahydrofuran. The resultant solution and 6.9 g (68 mmol) of triethylamine and 13.1 g (68 mmol) of p-toluenesulfonyl chloride added thereto were treated by following the procedure as described in SYNTHESIS EXAMPLE 3. Consequently, 7.1 g (65% in yield) of Coupler (62) was obtained.

Melting Point: 140° to 142° C.
Mass Analysis: 192 (M+), 136 (b.p.).
Nuclear Magnetic Resonance Spectrum (CDCl$_3$): 0.90 (6H, d, J=6), 1.55–1.90 (3H), 2.45 (3H, s), 2.90 (2H, brt, J=7), 5.60 (1H, s), 13.3 (1H).

SYNTHESIS EXAMPLE 11

Coupler (57) was synthesized using Method III as follows.

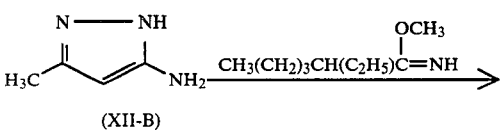

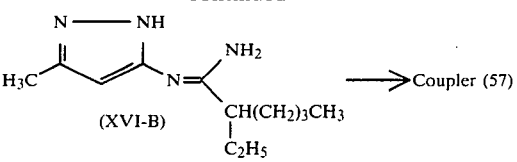

From 2-ethylhexanoyl chloride, 2-ethylhexanonitrile was synthesized by the method described in Org. Syn. Coll., Vol. 3, p. 490 (1955). This product was dissolved in 1 equivalent of methanol. The resultant solution was allowed to absorb 1 equivalent of dry hydrogen chloride gas at 0° C. When the absorbate was allowed to stand in a refrigerator at −5° C. for about 20 days, crystals of the methylimidate hydrochloride were precipitated. The mixture was combined with diethyl ether and then filtered to separate the crystals in a yield of 48%.

In 150 ml of methanol, 10 g (51.6 mmol) of the imidate hydrochloride and 5 g (51.5 mmol) of (XII-B) were stirred at 40° C. After about 7 hours of stirring, two spots were observed in TLC (using silica gel and an eluant obtained by mixing chloroform with ethanol in a ratio of 4:1 by vol.). The spot of lower polarity had the structure of (XIII). The solution and an excess amount of ammonium chloride added thereto were refluxed with heating for about 2 hours. Consequently, (XIII) vanished and (XVI) alone remained. The resultant reaction mixture was subjected to vacuum distillation to remove the methanol. The residue was combined with 50 ml of chloroform and 10 ml of methanol and the resultant mixture was filtered to remove insolubles. The filtrate was concentrated and purified with a small amount of silica gel in a column. Consequently, 8 g (70% in yield) of (XVI) in an oily state was obtained.

Nuclear Magnetic Resonance Spectrum (CDCl$_3$: CD$_3$OD=3:2): 0.7–1.2 (6H), 1.2–1.6 (4H), 1.6–2.1 (4H), 2.32 (3H, s), 2.80 (1H, quintet J=7), 5.70 (3H, broad), and 6.20 (1H, s).

In 50 ml of acetic acid, 2.6 g (12 mmol) of (XVI) was dissolved. At room temperature, 5.8 g (12 mmol) of lead tetraacetate was added incrementally to the resultant solution under a nitrogen atmosphere. After the addition, the resultant mixture was refluxed with heating for 3 hours. The resultant reaction mixture was subjected to vacuum distillation to remove the acetic acid, extracted three times, each time with a 30:1 by volume mixed solvent of chloroform and ethanol, washed with a saturated aqueous sodium bicarbonate solution and an aqueous sodium chloride solution, and dried with magnesium sulfate. The resultant reaction mixture was filtered, concentrated, and purified by silica gel column chromatography. Consequently, 0.15 g (5.7% in yield) of Coupler (57) was obtained.

Melting Point: 110° to 115° C.
Mass Analysis: 220 (M+), 155, 130.
Nuclear magnetic Resonance Spectrum (CDCl$_3$): 0.7–1.2 (6H), 1.2–1.55 (4H), 1.55–2.20 (4H), 2.45 (3H, s), 2.95 (1H, quintet, J=7), 5.62 (1H, s), and 12.6 (1H).

SYNTHESIS EXAMPLE 12

Coupler (58) was synthesized by Method II as follows.

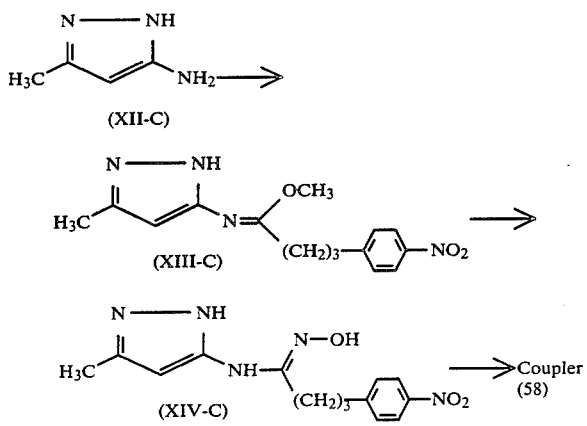

In 100 ml of toluene, 9.2 g (34 mmol) of trimethyl orhto-4-(p-nitrophenyl)butyrate and 5 g (51 mmol) of 3-amino-5-methyl pyrazole (XII-C) were refluxed with heating for 10 hours. The resultant mixture was subjected to vacuum distillation to remove the toluene. The (XIII-C) thus obtained in a crude form was dissolved in 100 ml of methanol. To the resultant solution, a methanol solution of hydroxylamine prepared from 3.5 g (50 mmol) of hydroxylamine hydrochloride as described in SYNTHESIS EXAMPLE 3 was added at 0° C. After this addition, the resultant mixture was stirred at room temperature for 1 hour. The stirred mixed solution was subjected to vacuum distillation to remove the solvent. When the residue after the distillation and 30 ml of dichloromethane added thereto were allowed to stand, crystals of (XIV-C) precipitated in the solution. Yield 6.7 g (65%), melting point 190° to 193° C. (decomposition).

In 500 ml of tetrahydrofuran (THF), 2 g (6.6 mmol) of (XIV-C) was dissolved. The resultant solution and 0.73 g (7.3 mmol) of triethylamine added thereto were stirred. Into the stirred mixture, a solution of 1.4 g (7.3 mmol) of p-toluenesulfonyl chloride in 50 ml of THF was gradually added. After this addition, the stirring of the mixture was continued for about 1 hour to induce precipitation of triethylamine hydrochloride salt. This mixture was filtered to separate the precipitate. The separated precipitate was washed with 150 ml of THF. The filtrate was refluxed with heating under a nitrogen atmosphere for about 7 hours and, thereafter, distilled under a vacuum to remove the THF. The residue was purified by silica gel chromatography. Consequently, 1.2 g (63% in yield) of Coupler (58) was obtained.

Melting Point: ~152° C.

Mass Analysis: 285 (M+), 149 (b.p.).

Nuclear Magnetic Resonance Spectrum (DMSO-d$_6$): 2.05 (2H, m), 2.45 (3H, s), 2.56–2.86 (4H, m), 5.60 (1H, s), 7.25 (2H, d, J=8.0), and 8.05 (2H, d, J=8.0).

SYNTHESIS EXAMPLE 13

Coupler (65) was sythesized starting with Coupler (58) via Couplers (59) and (61).

In 100 ml of isopropyl alcohol, 20 g (0.36 mol) of reduced iron, 1.4 g (28 mmol) of ammonium chloride, and 10 ml of water were vigorously sitrred and heated until the resultant mixture was refluxed. The resultant mixture and 0.3 ml of concentrated hydrochloric acid added thereto were refluxed with heating for 30 minutes. To the resluxed mixture, 15.2 g (53.2 mmol) of Coupler (58) was added incrementally over a period of 20 minutes. The resultant mixture was refluxed with heating for one hour. The refluxed mixture was filtered through celite and thoroughly washed with ethanol. The filtrate was concentrated, dissolved in a 2N HCl aqueous solution, and washed with ethyl acetate. The aqueous layer was neutralized with aqueous ammonia to induce precipitation and filtered to separate the precipitate. The separated precipitate was washed first with cold water and then with acetonitrile and, thereafter, dried. Consequently, 10.9 g (80% in yield) of Coupler (59) in a substantially pure state was obtained.

Melting Point: ~180° C.

Nuclear Magnetic Resonance Spectrum (DMSO-d$_6$): 1.90 (2H, br, quintet, J= ~7), 2.46 (3H, s), 2.3–2.8 (4H), 5.60 (1H, s), 6.55 (2H, d, J=8.5), and 6.93 (2H, d, J=8.5).

Coupler (59) in the amount of 3.6 g (14.0 mol) and a mixed solvent of 30 ml of N,N-dimethylacetamide and 60 ml of acetonitrile added thereto were refluxed with heating. Into the resultant mixture, a solution of 6.1 g (15.4 mmol) of the acid chloride, [(t-C$_5$H$_{11}$)$_2$-C$_6$H$_3$OCH(n-C$_6$H$_{13}$)COCl], in 20 ml of acetonitrile was added dropwise over a period of 20 minutes. The resultant mixture was refluxed with heating for 30 minutes. The hot mixture was cooled, poured into 300 ml of cold water, and extracted using ethyl acetate. The extract was washed with a saturated sodium chloride aqueous solution, dried over anhydrous magnesium sulfate, concentrated, and subjected to silica gel column chromatography. Consequently, 7.0 g (81% in yield) of Coupler (61) was obtained.

Nuclear Magnetic Resonance Spectrum (CDCl$_3$): 0.50–1.00 (7H, m), 1.00–2.15 (30H, m), 2.45 (3H, s), 2.46–2.80 (4H, m), 4.68 (1H, t, J=6.5), 5.60 (1H, s), 6.88–7.33 (6H, m), 7.66 (1H, d, J=9.0), and 7.88 (1H, br, s).

Coupler (61) in the amount of 3.1 g (5.00 mmol) and 25 ml of acetic acid added thereto were stirred at room temperature. Into the resultant solution, 586 mg (5.00 mmol) of isoamyl nitrite was added dropwise. The resultant mixture was stirred for one hour. The stirred mixture was gradually added to 300 ml of cold water to induce precipitation. The precipitate was separated by filtering the mixture and then washed with cold water. The precipitate was dried under a vacuum. Consequently, 2.9 g (91% in yield) of the 7-nitroso derivative in a solid state was obtained.

The 7-nitroso derivative in the amount of 2.9 g (4.5 mmol) was dissolved in 50 ml of ethanol. The solution was heated under a nitrogen atmosphere until it refluxed. To the refluxed solution, a solution of 4.27 g (22.5 mmol) of stannous chloride in 10 ml of concentrated hydrochloric acid was added dropwise over a period of 10 minutes. The resultant mixture was refluxed with heating for 30 minutes, then cooled, poured into 150 ml of cold water, and extracted using ethyl acetate. The ethyl acetate layer was dried over anhydrous magnesium sulfate and then concentrated to dryness. The dry mass thus obtained and 100 ml of toluene and 0.49 g (5.0 mmol) of 2,5-dimethyl-1,3,4-oxadiazole added thereto were refluxed with heating for about 5 hours. The refluxed mixture was poured into 250 ml of cold water and extracted using ethyl acetate. The ethyl acetate layer was dried over anhydrous magnesium sulfate, concentrated, and subjected to silica gel column chromatography. Consequently, 2.2 g (70% in yield) of Coupler (65) in a solid state was obtained.

Melting Point: ~120° C.

Nuclear Magnetic Resonance Spectrum (CDCl$_3$): 0.48–1.00 (7H, m), 1.05–2.20 (30H, m), 2.43 (3H, s), 2.46 (6H, s), 2,46–2.80 (4H, m), 4.67 (1H, t, J=6.5), 6.60 (1H, d, J=8.5), 6.90–7.35 (6H, m), and 7.85 (1H, s).

Light-fastness of the magenta color image formed from the magenta coupler according to the present invention can be improved by using it together with a color image stabilizing agent represented by the following general formula:

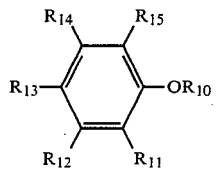

wherein $R_{10}$ represents a hydrogen atom, an alkyl group, an aryl group or a heterocyclic group; $R_{11}$, $R_{12}$, $R_{14}$ and $R_{15}$ each represents a hydrogen atom, a hydroxy group, an alkyl group, an aryl group, an alkoxy group or an acylamino group; $R_{13}$ represents an alkyl group, a hydroxy group, an aryl group or an alkoxy group; $R_{10}$ and $R_{11}$ may be combined with each other to form a 5-membered or 6-membered ring and in such a case, $R_{13}$ represents a hydroxy group or an alkoxy group; $R_{10}$ and $R_{11}$ may be combined with each other to form a methylenedioxy ring; and $R_{13}$ and $R_{14}$ may be combined with each other to form a 5-membered hydrocarbon ring and in such a case, $R_{10}$ represents an alkyl group, an aryl group or a heterocyclic group. In the substituents $R_{10}$, $R_{11}$, $R_{12}$, $R_{13}$, $R_{14}$ and $R_{15}$, an alkyl group or an alkyl moiety contains 1 to 22 carbon atoms, and an aryl group or an aryl moiety contains 6 to 22 carbon atoms.

The color image stabilizing agents further include those described in U.S. Pat. Nos. 3,935,016, 3,982,944 and 4,254,216, Japanese Patent Application (OPI) Nos. 21004/80 and 145530/79, British Patent Application (OPI) Nos. 2,077,455A and 2,062,888A, U.S. Pat. Nos. 3,764,337, 3,432,300, 3,574,627 and 3,573,050, Japanese Patent Application (OPI) Nos. 152225/77, 20327/78, 17729/78 and 6321/80, British Pat. No. 1,347,556, British Patent Application (OPI) No. 2,066,975A, Japanese Patent Publication Nos. 12337/79 and 31625/73 and U.S. Pat. No. 3,700,455, etc.

A preferred embodiment of the present invention is a silver halide color photographic light-sensitive material containing the coupler according to the present invention.

The coupler according to the present invention can be employed by incorporating into a photographic light-sensitive material or by adding to a color developing solution. In case of incorporating the coupler into a photographic light-sensitive material, a suitable amount thereof ranges from $2 \times 10^{-3}$ to $5 \times 10^{-1}$ mole, preferably from $1 \times 10^{-2}$ to $5 \times 10^{-1}$ mole, per mole of silver halide. When a polymer coupler is used, an amount of the polymer coupler added is adjusted so that an amount of the color forming portion thereof is within the above-described range. On the other hand, when the coupler is added to a color developing solution, it is used in an amount of 0.001 to 0.1 mole, preferably 0.01 to 0.05 mole, per 1,000 ml of the solution.

Conventional couplers which can be employed in the present invention in addition to the couplers according to the present invention include dye forming couplers as described below, that is, compounds capable of color forming upon oxidative coupling with an aromatic primary amine developing agent (e.g., phenylenediamine derivatives, aminophenol derivatives, etc.) in color development processing. More specifically, suitable examples of conventional magenta couplers which can be used include 5-pyrazolone couplers, pyrazolobenzimidazole couplers, cyanoacetylcumarone couplers, open-chain acylacetonitrile couplers, etc. When the magenta coupler according to the present invention is used together with a conventional magenta coupler, the amount of the magenta coupler according to the present invention is at least 30 mole%, preferably at least 60 mole%, of the total amount of magenta coupler. Suitable examples of yellow couplers which can be used include acylacetamide couplers (e.g., benzoylacetanilides, pivaloylacetanilides, etc.), etc. Suitable examples of cyan couplers which can be used include naphthol couplers, phenol couplers, etc. Among these couplers, those which are non-diffusible by containing a hydrophobic group referred to as a ballast group in the molecule thereof, or polymer couplers are preferably employed. These couplers may be either 4-equivalent or 2-equivalent per silver ion. Further, colored couplers having a color correction effect, or couplers capable of releasing a development inhibitor with the advance of development (the so-called DIR couplers) can be employed.

Furthermore, non-color forming DIR coupling compounds which can provide colorless products upon the coupling reaction and release development inhibitors can be employed in place of or in addition to ordinary DIR couplers.

Two or more kinds of the above-described couplers and the like can be incorporated together in the same layer for the purpose of satisfying characteristics required to the light-sensitive material, or the same coupler compound may naturally be added to two or more layers.

In order to incorporate the coupler into a silver halide emulsion layer, known methods, e.g., the method as described in U.S. Pat. No. 2,322,027, etc., can be employed. Specifically, the coupler is dissolved in an organic solvent having a high boiling point, for example, phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate, etc.), citric acid esters (e.g., tributyl acetylcitrate, etc.), benzoic acid esters (e.g., octylbenzoate, etc.), alkylamides (e.g., diethyllaurylamide, etc.), fatty acid esters (e.g., dibutoxyethyl succinate, diethyl azelate, etc.), trimesic acid esters (e.g., tributyl trimesate, etc.), etc., or in an organic solvent having a boiling point of about 30° C. to 150° C., for example, lower alkyl acetates (e.g., ethyl acetate, butyl acetate, etc.), ethyl propionate, secondary butyl alcohol, methyl isobutyl ketone, β-ethoxyethyl acetate, methyl cellosolve acetate, etc., and then the solution is dispersed into a hydrophilic colloid. The above-described organic solvents having a high boiling point and above-described organic solvents having a low boiling point may be used as mixtures.

Further the dispersing method utilizing a polymeric material as described in Japanese Patent Publication No. 39853/76 and U.S. Pat. No. 4,203,716 can also be employed.

When the coupler contains an acid group such as a carboxylic acid group, a sulfonic acid group, etc., it is incorporated into a hydrophilic colloid in the form of an alkaline aqueous solution.

For the polymer coupler, an oleophilic polymer coupler prepared by polymerization of a monomeric coupler is recovered, dissolved again in an organic solvent and dispersed in a hydrophilic colloid in the form of a latex; or a solution of an oleophilic polymer coupler prepared by polymerization is directly dispersed in the form of a latex. Further, a polymer coupler latex prepared by an emulsion polymerization method or a polymer coupler latex having a layer structure is directly added to a gelatino silver halide emulsion.

Water-soluble polymer couplers can be prepared by the method as described in U.S. Pat. Nos. 3,155,510, 3,221,552 and 3,299,013, Research Disclosure, No. 19033, etc. With respect to the polymer coupler latex, a method in which an oleophilic polymer coupler is dispersed in an aqueous gelatin solution in the form of a latex as described in U.S. Pat. No. 3,451,820, etc., or a method in which a polymer coupler latex prepared by an emulsion polymerization method is directly added to a gelatino silver halide emulsion as described in U.S. Pat. Nos. 4,080,211, 3,370,952, 3,926,436 and 3,767,412, British Pat. No. 1,247,688, etc., is used.

These methods can be applied to the preparation of both monopolymers and copolymers.

It is advantageous that photographic color couplers are used so as to provide images of neutral gray. It is preferred that cyan dyes formed from cyan couplers exhibit their maximum absorption bands in the wavelength range from about 600 nm to 720 nm, magenta dyes formed from magenta couplers exhibit their maximum absorption bands in the wavelength range from about 500 nm to 580 nm, and yellow dyes formed from yellow couplers exhibit their maximum absorption bands in the wavelength range from about 400 nm to 480 nm.

The light-sensitive material prepared using the present invention may contain, as a color fog preventing agent, hydroquinone derivatives, aminophenol derivatives, gallic acid derivatives, ascorbic acid derivatives and the like. Specific examples of the color fog preventing agent which can be used include those described in U.S. Pat. Nos. 2,306,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110337/75 and 146235/77, Japanese Patent Publication No. 23813/75, etc.

The light-sensitive material prepared using the present invention may contain an ultraviolet ray absorbing agent in a hydrophilic colloid layer thereof. Suitable examples of such an ultraviolet ray absorbing agent include benzotriazole compounds substituted with an aryl group (e.g., those described in U.S. Pat. No. 3,533,794, etc.), 4-thiazolidone compounds (e.g., those described in U.S. Pat. Nos. 3,314,794 and 3,352,681, etc.), benzophenone compounds (e.g., those described in Japanese Patent Application (OPI) No. 2784/71, etc.), cinnamic acid ester compounds (e.g., those described in U.S. Pat. Nos. 3,705,805 and 3,707,375, etc.), butadiene compounds (e.g., those described in U.S. Pat. No. 4,045,229, etc.) and benzoxazole compounds (e.g., those described in U.S. Pat. No. 3,700,455, etc.), etc. In addition, those described in U.S. Pat. No. 3,499,762 and those described in Japanese Patent Application (OPI) No. 48535/79 can also be employed. Further, couplers which have ultraviolet ray absorbing abilities (e.g., α-naphthol type cyan dye forming couplers, etc.) and polymers which have ultraviolet ray absorbing abilities may be employed. These ultraviolet ray absorbing agents may be mordanted in a specific layer(s).

The light-sensitive material prepared using the present invention may contain a water-soluble dye in a hydrophilic colloid layer thereof as a filter dye or for purpose of preventing irradiation or other various purposes. Suitable examples of such a dye include oxonol dyes, hemioxonol dyes, styryl dyes, merocyanine dyes, cyanine dyes and azo dyes, etc. Of these dyes, oxonol dyes, hemioxonol dyes and merocyanine dyes are useful. Specific examples of the dye which can be used include those described in British Pat. Nos. 584,609 and 1,177,429, Japanese Patent Application (OPI) Nos. 85130/73, 99620/74, 114420/74 and 108115/77, U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352, etc.

The photographic emulsion which can be used in the present invention may be spectrally sensitized with methine dyes or other dyes. Suitable dyes which can be used include cyanine dyes, merocyanine dyes, complex cyanine dyes, complex merocyanine dyes, holopolar cyanine dyes, hemicyanine dyes, styryl dyes and hemioxonol dyes. Of these dyes, especially useful dyes are those belonging to cyanine dyes, merocyanine dyes or complex merocyanine dyes. Any nucleus which is conventionally used in cyanine dyes as a basic heterocyclic nucleus is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted.

The merocyanine dyes and the complex merocyanine dyes can contain 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, etc., as a nucleus having a ketomethylene structure.

Specific examples of useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese Patent Publication Nos. 14030/69 and 24844/77, etc.

These sensitizing dyes can be employed individually or in combination. Combinations of sensitizing dyes are often employed for the purpose of supersensitization. Typical examples of supersensitizing combinations are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Application (OPI) Nos. 110618/77 and 109925/77, etc.

The sensitizing dye can be used in the emulsion together with dyes which themselves do not have a spectrally sensitizing function but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721, etc.), aromatic organic acid-formaldehyde condensates (e.g., those described in U.S. Pat. No. 3,743,510, etc.), cadmium salts, azaindene compounds, etc., can be used. Particularly useful combinations are those disclosed in U.S. Pat. Nos. 3,615,613, 3,615,641, 3,617,295 and 3,635,721.

Photographic processing of the light-sensitive material according to the present invention can be carried out using any known methods. Further, known processing solutions can be used. The processing temperature is generally selected from a range of 18° C. to 50° C., but temperatures lower than 18° C. or higher than 50° C. may be employed. Either a development processing for forming silver images (black-and-white photographic processing) or a color photographic processing comprising a development processing for forming dye images may be employed depending upon the purpose.

A color developing solution is generally an alkaline aqueous solution containing a color developing agent. As a color developing agent, known primary aromatic amine developing agents such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc.) can be used.

In addition, those described in L. F. A. Mason, *Photographic Processing Chemistry*, pages 226 to 229, Focal Press, (1966), U.S. Pat. Nos. 2,193,015 and 2,592,364, Japanese Patent Application (OPI) No. 64933/73, etc., can be used.

The color developing solution can also contain pH buffering agents such as sulfites, carbonates, borates and phosphates of alkali metals, etc.; development restrainers or antifogging agents such as bromides, iodides or organic antifogging agents, etc. In addition, if desired, the color developing solution may contain water softeners; preservatives such as hydroxylamine, etc.; organic solvents such as benzyl alcohol, diethylene glycol, etc.; development accelerators such as polyethylene glycol, quaternary ammonium salts, amines, etc.; dye forming couplers; competing couplers; fogging agents such as sodium borohydride, etc.; auxiliary developing agents such as 1-phenyl-3-pyrazolidone; viscosity imparting agents; chelating agents of polycarbonylic acid type as described in U.S. Pat. No. 4,083,723; antioxidants as described in West German Patent Application (OLS) No. 2,622,950; etc.

After color development, the photographic emulsion layers are generally subjected to a bleach processing. Bleach processing can be carried out simultaneously with fixing or separately therefrom. Suitable examples of the bleaching agents which can be used include compounds of polyvalent metals such as iron (III), cobalt (III), chromium (VI), copper (II), etc., peracids, quinones, nitroso compounds, etc. Specific examples include ferricyanides; bichromates; organic complex salts of iron (III) or cobalt (III) with aminopolycarboxylic acids such as ethylenediaminetetraacetic acid, nitrilotriacetic acid, 1,3-diamino-2-propanoltetraacetic acid, etc., or organic acids such as citric acid, tartaric acid, malic acid, etc.; persulfates; permanganates; nitrosophenol, etc. Of these compounds, potassium ferricyanide, sodium ethylenediaminetetraacetato iron (III), and ammonium ethylenediaminetetraacetato iron (III) are particularly useful. Ethylenediaminetetraacetato iron (III) complex salts are useful both in a bleaching solution and in a mono-bath bleach-fixing solution.

To a bleaching solution or a bleach-fixing solution, bleaching accelerators as described in U.S. Pat. Nos. 3,042,520 and 3,241,966, Japanese Patent Publication Nos. 8506/70 and 8836/70, etc.; thiol compounds as described in Japanese Patent Application (OPI) No. 65732/78, and other various additives can be added.

The silver halide emulsion used in the present invention is prepared generally by mixing a solution of a water-soluble silver salt (e.g., silver nitrate) with a solution of a water-soluble halide (e.g., potassium bromide) in the presence of a solution of a water-soluble polymer (e.g., gelatin). Silver halides which can be used include not only silver chloride and silver bromide, but also mixed silver halides such as silver chlorobromide, silver iodobromide, silver chloroiodobromide, etc. A mean grain size of silver halide grains produced (the grain size refers to the diameter of a grain when it is spherical or similar to sphere in the shape, or the edge length when it is cubic, and the mean grain size is determined on the basis of the projected areas) is preferably $2\mu$ or less, especially $0.4\mu$ or less. The distribution of the grain size can be either narrow or broad.

These silver halide grains may have crystals in the form of a cube, an octahedron, or a composite form thereof, etc.

Also, two or more silver halide photographic emulsions which are produced separately may be used in the form of a mixture. Further, silver halide grains having a uniform crystal structure, silver halide grains in which the inner portion and the other portion have different layer structures, or silver halide grains of the so-called conversion type as described in British Pat. No. 635,841, U.S. Pat. No. 3,622,318, etc., may be employed. Moreover, either silver halide grains in which a latent image is predominantly formed at the surface or grains in which a latent image is predominantly formed inner portion thereof can be used. These photographic emulsions are described in C. E. K. Mees, *The Theory of the Photographic Process*, Macmillan Co., P. Glafkides, *Chimie Photographique*, Paul Montel Co. (1957), etc. These photographic emulsions can be prepared using the methods as described in, e.g., P. Glafkides, *Chimie et Physique Photographique*, Paul Montel Co. (1967), G. F. Duffin, *Photographic Emulsion Chemistry*, The Focal Press (1966), V. L. Zelikman et al., *Making and Coating Photographic Emulsion*, The Focal Press (1964), etc. Any of an acidic process, a neutral process or an ammonia process may be used for the preparation of the photographic emulsions. Suitable methods for reacting a water-soluble silver salt with a water-soluble halide include, e.g., a single jet method, a double jet method or a combination thereof.

Also, a method in which silver halide grains are formed in the presence of an excess of silver ions (the so-called reversal mixing method) can be employed in the present invention. Further, the so-called controlled double jet method, in which the pAg in a liquid phase wherein silver halide grains are formed is maintained at a constant, may be also employed. According to this method, a silver halide emulsion having a regular crystal form and almost uniform grain sizes can be obtained.

A mixture of two or more kinds of silver halide emulsions prepared separately may be employed.

In a process of forming silver halide grains of physical ripening thereof, cadmium salts, zinc salts, lead salts, thallium salts, iridium salts or complex salts thereof, rhodium salts or complex salts thereof, iron salts or complex salts thereof, etc., may be present.

Removal of the soluble salts from the silver halide emulsion is, in general, carried out after the formation of the silver halide grains or after physical ripening. The removal can be effected using the noodle washing method which has been known from old times and comprises gelling the gelatin, or using a sedimentation process (thereby causing flocculation in the emulsion) using a polyvalent anion-containing inorganic salt (e.g., sodium sulfate, etc.), an anionic surface active agent, an anionic polymer (e.g., polystyrenesulfonic acid, etc.), or a gelatin derivative (e.g., an aliphatic acylated gelatin, an aromatic acylated gelatin, an aromatic carbamoylated gelatin, etc.). The removal of the soluble salts from the silver halide emulsion may be omitted.

The silver halide emulsion used in the present invention can be the so-called primitive emulsion without application of chemical sensitization. However, it is usually chemically sensitized. Chemical sensitization can be carried out using the methods as described in P. Glafkides, supra, V. L. Zelikman et al., supra, or H. Frieser, *Die Grundlagen der Photographischen Prozesse mit Silberhalogeniden*, Akademische Verlagsgesellschaft (1968).

The photographic emulsion layers and other hydrophilic colloid layers which constitute the light-sensitive material according to the present invention may contain various kinds of surface active agents as coating aids or for other various purposes, for example, prevention of charging, improvement of slipping property, emulsifying dispersion, prevention of adhesion, improvement of photographic characteristics (e.g., acceleration of development, high contrast, sensitization, etc.), etc.

Examples of suitable surface active agents include nonionic surface active agents, for example, saponin (steroid type), alkylene oxide derivatives (e.g., polyethylene glycol, polyethylene glycol/polypropylene glycol condensates, polyethylene glycol alkyl ethers or polyethylene glycol alkylaryl ethers, polyethylene glycol esters, polyethylene glycol sorbitan esters, polyalkylene glycol alkylamines or amides, polyethylene oxide adducts of silicones, etc.), glycidol derivatives (e.g., alkenylsuccinic acid polyglycerides, alkylphenol polyglycerides, etc.), fatty acid esters of polyhydric alcohols, alkyl esters of sugar, etc.; anionic surface active agents containing acidic groups such as a carboxy group, a sulfo group, a phospho group, a sulfuric acid ester group, a phosphoric acid ester group, etc., for example, alkylcarboxylates, alkylsulfonates, alkylbenzenesulfonates, alkylnaphthalenesulfonates, alkylsulfuric acid esters, alkylphosphoric acid esters, N-acyl-N-alkyltaurines, sulfosuccinic acid esters, sulfoalkylpolyoxyethylene alkylphenyl ethers, polyoxyethylene alkylphosphoric acid esters, etc.; amphoteric surface active agents, for example, amino acids, aminoalkylsulfonic acids, aminoalkylsulfuric acid esters, aminoalkylphosphoric acid esters, alkylbetaines, amineoxides, etc.; and cationic surface active agents, for example, alkylamine salts, aliphatic or aromatic quaternary ammonium salts, heterocyclic quaternary ammonium salts (e.g., pyridinium, imidazolium, etc.), aliphatic or heterocyclic phosphonium or sulfonium salts, etc.

The present invention will be explained in greater detail with reference to the following examples, but the present invention should not be construed as being limited thereto.

EXAMPLE 1

1.1 millimol of each of Coupler (1) according to the present invention and Comparison Coupler A represented by the chemical structure formula shown below was dissolved in 10 ml of ethanol. In the solution, 1.3 millimole of 4-N-ethyl-N-(2-methanesulfonamidoethyl)-amino-2-methylaniline monosulfate, which is a color developing agent, was suspended. Then, an aqueous solution containing 12.9 millimole of anhydrous sodium carbonate dissolved in 5 ml of water was added thereo and the mixture was stirred at room temperature. To the mixture solution, 10 ml of an aqueous solution containing 2.4 millimole of potassium persulfate dissolved was gradually added dropwise.

After thoroughly stirring for 1 hour at room temperature, the reaction mixture was subjected to an extraction treatment by adding 50 ml of ethyl acetate and 30 ml of water. The ethyl acetate layer was washed thoroughly with a saturated sodium chloride aqueous solution and then the solvent was removed therefrom. The residue was separated using silica gel column chromatography. The eluate used was ethyl ether. The NMR spectrum of the magenta dye formed from Coupler (1) according to the present invention measured in heavy chloroform (CDCl$_3$) was as follows:

1.24 (3H, t, J=7.2), 2.45 (3H, s), 2.52 (6H, s), 2.98 (3H, s), 3.24–3.78 (6H), 4.64 (1H, brt, J=7), 6.60–6.80 (2H), 8.84 (1H, d, J=9.0).

The absorptions underlined correspond to four methyl groups and thus the structure of the magenta dye is confirmed to be the formula shown below. The melting point of the magenta dye is 244° to 245° C.

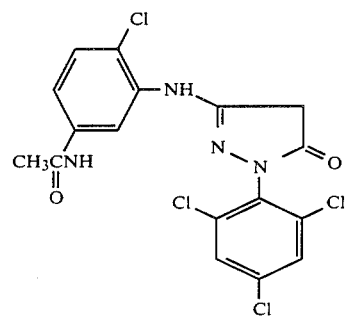

Comparison Coupler A

Magenta Dye B

-continued

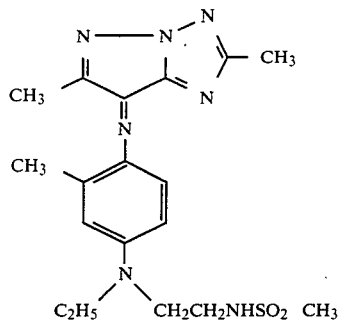

(wherein the methyl groups in the circles correspond to the methyl groups exhibiting the above-described chemical shifts in the NMR spectrum).

Visible absorption spectra of Magenta Dye B and the magenta dye formed from Comparison Coupler A in ethyl acetate are shown in the FIGURE. In the FIGURE the absorption spectral curves are normalized taking the maximum density as 1.0 for comparison.

It is apparent from the FIGURE that the dye obtained from the coupler according to the present invention has the $\lambda_{max}$ coincident with that of the dye formed from Comparison Coupler A, no subsidiary absorption in the range from 400 nm to 430 nm and sharply cut absorption curve at the longer wavelength side. Therefore, the coupler according to the present invention is advantageous in color reproduction when it is employed in a color photographic light-sensitive material.

EXAMPLE 2

13 g of Comparison Coupler C shown below was dissolved together with 15 ml of trioctyl phosphate and 15 ml of ethyl acetate. The resulting solution was added to 100 g of a 10% aqueous gelatin solution containing sodium di-sec-butylnaphthalenesulfonate, and the mixture was stirred and dispersed by means of a homogenizer to prepare a dispersion. The dispersion thus-prepared was mixed with 300 g of a green-sensitive silver chlorobromide emulsion (containing 13.5 g of silver, and having a bromide content of 45 mol% and a chloride content of 55 mol%) and thereto was added sodium dodecylbenzenesulfonate as a coating aid and 2-hydroxy-4,6-dichloro-s-triazine as a hardener. The mixture was coated on a cellulose triacetate support to form an emulsion layer. Further, a gelatin coating solution was applied to the emulsion layer as a protective layer at a coverage of 1 g gelatin per square meter, and dried. The light-sensitive material thus-prepared was designated Film A.

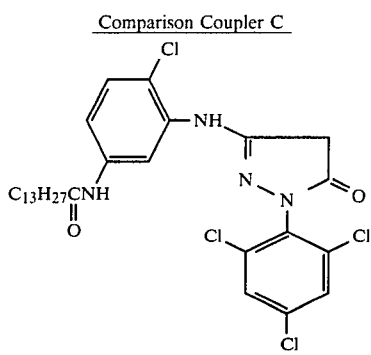

Comparison Coupler C

Also, Film B was prepared in the same manner as described for Film A except using 9.9 g of Coupler (5) according to the present invention in place of Comparison Coupler C.

Further, Film C was prepared in the same manner as described for Film A except that 10.6 g of Coupler (13) according to the present invention was used in place of Comparison Coupler C and the amount of the green-sensitive silver chlorobromide emulsion was reduced to 200 g.

Films A to C described above were exposed to light using a sensitometer under the condition of 1,000 lux·1 sec. and subjected to the following development processing.

| Processing Step | Temperature (°C.) | Time |
|---|---|---|
| Development | 33 | 3 min 30 sec |
| Bleach-Fixing | 33 | 1 min 30 sec |
| Washing | 28–35 | 3 min |

The processing solutions used have the following compositions.

| Developing Solution | |
|---|---|
| Benzyl Alcohol | 15 ml |
| Diethylenetriaminepentaacetic Acid | 5 g |
| Potassium Bromide | 0.4 g |
| Sodium Sulfite | 5 g |
| Sodium Carbonate | 30 g |
| Hydroxylamine Sulfate | 2 g |
| 4-Amino-3-methyl-N—ethyl-N—β-(methane sulfonamido)ethylaniline Sesquisulfate Monohydrate | 4.5 g |
| Water to make | 1,000 ml (pH = 10.1) |
| Bleach-Fixing Solution | |
| Ammonium Thiosulfate (70 wt %) | 150 ml |
| Sodium Sulfite | 5 g |
| Sodium Ethylenediaminetetraacetato Iron (III) | 40 g |
| Ethylenediaminetetraacetic Acid | 4 g |
| Water to make | 1,000 ml (pH = 6.8) |

The densities of dye images after the color development processing were measured using a Macbeth densitometer with a Status AA filter. Further, the absorption spectra of the dye images were measured. It was found that the absorption of each dye image of the present invention on the film had no subsidiary absorption and the absorption curve on the longer wavelength side was cut sharply similar to the results of Example 1. The color forming characteristics are shown in the following Table.

TABLE

| Film | Coupler | Mole Ratio of Ag/Cp | Maximum Density | Maximum Absorption Wavelength (nm) | Subsidiary Absorption (density at 420 nm)* |
|---|---|---|---|---|---|
| A | Comparison Coupler C | 6 | 2.62 | 535 | 0.137 |
| B | Coupler (5) (Present Invention) | 6 | 2.60 | 536 | 0.049 |
| C | Coupler (13) (Present Invention) | 4 | 3.20 | 536 | 0.048 |

*The density was obtained by taking the maximum density as 1.0.

The results in the Table above show that the couplers according to the present invention provide sufficiently high color densities compared with a conventional 5-pyrazolone type coupler. In particular, a 2-equivalent coupler represented by Coupler (13) provides a high color density in spite of a small amount of silver coated.

In addition, the subsidiary absorptions in the range around 420 nm were extremely low with respect to the couplers according to the present invention in comparison with that of the comparison coupler. Therefore, excellent color reproduction can be achieved by the couplers according to the present invention.

While the invention has been described in detail and with reference to specific embodiments thereof, it will be apparent to one skilled in the art that various changes and modifications can be made therein without departing from the spirit and scope thereof.

What is claimed is:

1. A method of forming a color image comprising developing a silver halide photographic light-sensitive material with a developing solution containing an aromatic primary amine in the presence of a coupler represented by general formula (I) and/or a polymer coupler having a repeating unit derived from a vinyl monomer containing a part represented by general formula (I) in its molecule:

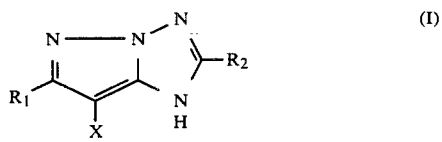

wherein $R_1$ and $R_2$ are independently a hydrogen atom or a substituent; and X is a hydrogen atom or a group capable of being released upon coupling.

2. A method of forming a color image as claimed in claim 1, wherein $R_1$ and $R_2$ are independently a hydrogen atom, a halogen atom, an aliphatic residue, an aryl group, a heterocyclic group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclicoxy group, an acyloxy group, a carbamoyloxy group, a silyloxy group, an aryloxycarbonylamino group, an imido group, a heterocyclicthio group, a sulfinyl group, a phosphonyl group, an aryloxycarbonyl group, an acyl group or an alkoxycarbonyl group.

3. A method of forming a color image as claimed in claim 1, wherein X is a hydrogen atom, a halogen atom, a carboxy group or a group capable of being released upon coupling which is bonded to the carbon atom of the coupling position through an oxygen atom, a nitrogen atom, a carbon atom or a sulfur atom.

4. A method of forming a color image as claimed in claim 1, wherein $R_1$, $R_2$ or X are independently a divalent group for forming a bis coupler.

5. A method of forming a color image as claimed in claim 1, wherein $R_1$ or $R_2$ are independently a simple bond or a linking group through which the part represented by the general formula (I) is bonded to a vinyl group of the vinyl monomer.

6. A method of forming a color image as claimed in claim 2, wherein the aliphatic residue represented by $R_1$ or $R_2$ is a straight chain or branched chain alkyl group having from 1 to 32 carbon atoms, an aralkyl group, an alkenyl group, an alkinyl group or a cycloalkyl group and each of which may be substituted with a substituent bonded through an oxygen atom, a nitrogen atom, a sulfur atom or a carbonyl group, a hydroxy group, an amino group, a nitro group, a carboxy group, a cyano group or a halogen atom.

7. A method of forming a color image as claimed in claim 3, wherein X represents a hydrogen atom, a halogen atom, a carboxy group, a group bonded to the coupling position through an oxygen atom, a group bonded to the coupling position through a nitrogen atom, a group bonded to the coupling position through a sulfur atom or a group bonded to the coupling position through a carbon atom.

8. A method of forming a color image as claimed in claim 4, wherein the divalent group for forming a bis coupler represented by $R_1$ or $R_2$ is a substituted or unsubstituted alkenylene group, a substituted or unsubstituted phenylene group, a group of the formula —NH—CO—$R_3$—CONH— (wherein $R_3$ represents a substituted or unsubstituted alkylene group or a substituted or unsubstituted phenylene group) or a group of the formula —S—$R_3$—S— (wherein $R_3$ is the same meaning as defined above).

9. A method of forming a color image as claimed in claim 5, wherein the linking group represented by $R_1$ or $R_2$ is a substituted or unsubstituted alkylene group, a substituted or unsubstituted phenylene group, —NH—CO—, —CONH—, —O—, —OCO—, an aralkylene group or a combination thereof.

10. A method of forming a color image as claimed in claim 1, wherein the polymer coupler is a homopolymer.

11. A method of forming a color image as claimed in claim 1, wherein the polymer coupler is a copolymer.

12. A method of forming a color image as claimed in claim 11, wherein the copolymer contains a repeating unit derived from a non-color-forming ethylenic monomer which does not couple with the oxidation product of an aromatic primary amine developing agent.

13. A method of forming a color image as claimed in claim 12, wherein the non-color-forming monomer is an acrylic acid, an ester of acrylic acid, an amide of acrylic acid, a vinyl ester, an acrylonitrile, a methacrylonitrile, an aromatic vinyl compound, itaconic acid, citraconic acid, crotonic acid, vinylidene chloride, a vinyl alkyl ether, maleic acid, maleic anhydride, an ester of maleic acid, N-vinyl-2-pyrrolidone, N-vinyl pyridine or 2- or 4-vinyl pyridine.

14. A method of forming a color image as claimed in claim 1, wherein the polymer coupler is a latex.

15. A method of forming a color image as claimed in claim 1, wherein the color image is formed in the presence of a compound represented by the following general formula:

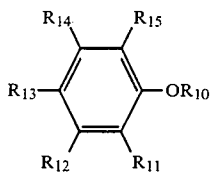

wherein $R_{10}$ represents a hydrogen atom, an alkyl group, an aryl group or a heterocyclic group; $R_{11}$, $R_{12}$, $R_{14}$ and $R_{15}$ each represents a hydrogen atom, a hydroxy group, an alkyl group, an aryl group, an alkoxy group or an acylamino group; $R_{13}$ represents an alkyl group, a hydroxy group, an aryl group or an alkoxy group; $R_{10}$ and $R_{11}$ may be combined with each other to form a 5-membered or 6-membered ring and in such a case $R_{13}$ represents a hydroxy group or an alkoxy group, $R_{10}$ and $R_{11}$ may be combined with each other to form a methylenedioxy ring; and $R_{13}$ and $R_{14}$ may be combined with each other to form a 5-membered hydrocarbon ring and in such a case $R_{10}$ represents an alkyl group, an aryl group or a heterocyclyl group.

16. A method of forming a color image as claimed in claim 1, wherein the coupler is present in the silver halide photographic light-sensitive material.

17. A method of forming a color image as claimed in claim 1, wherein the coupler is present in the developing solution.

18. A method of forming a color image as claimed in claim 1, wherein the coupler is present in an amount of from $2 \times 10^{-3}$ to $5 \times 10^{-1}$ mole per mole of silver halide.

19. A method of forming a color image as claimed in claim 17, wherein the coupler is present in an amount of from 0.001 to 0.1 mole per 1,000 ml of the developing solution.

20. A silver halide photographic light-sensitive material comprising a support having thereon a silver halide emulsion layer containing a coupler represented by the general formula (I) and/or a polymer coupler having a repeating unit derived from a vinyl monomer containing a part represented by general formula (I) in its molecule:

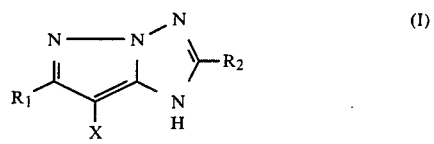

wherein $R_1$ and $R_2$ are independently a hydrogen atom or a substituent; and X represents a hydrogen atom or a group capable of being released upon coupling.

21. A silver halide photographic light-sensitive material as claimed in claim 20, wherein the silver halide emulsion layer is a green-sensitive silver halide emulsion layer.

22. A silver halide photographic light-sensitive material as claimed in claim 21, wherein the photographic light-sensitive material further comprises a blue-sensitive silver halide emulsion layer containing a yellow color image forming coupler and a red-sensitive silver halide emulsion layer containing a cyan color image forming coupler.

23. A silver halide photographic light-sensitive material as claimed in claim 20, wherein the coupler is present in the silver halide emulsion layer in an amount of from $2 \times 10^{-3}$ to $5 \times 10^{-1}$ mole per mole of silver halide.

24. A silver halide photographic light-sensitive material as claimed in claim 22, wherein the coupler is present in the silver halide emulsion layer in an amount of from $2 \times 10^{-3}$ to $5 \times 10^{-1}$ mole per mole of silver halide.

* * * * *